US008530520B2

(12) United States Patent
Atasoylu et al.

(10) Patent No.: US 8,530,520 B2
(45) Date of Patent: Sep. 10, 2013

(54) CYCLOALKYL-DIONE DERIVATIVES AND METHODS OF THEIR USE

(75) Inventors: Onur Atasoylu, Izmir (TR); Carlo Ballatore, Philadelphia, PA (US); Kurt R. Brunden, Media, PA (US); Longchuan Huang, Philadelphia, PA (US); Donna M. Huryn, Allentown, NJ (US); Michael James, Philadelphia, PA (US); Virginia M. Y. Lee, Philadelphia, PA (US); Francesco Piscitelli, Strongoli Marina (IT); Amos B. Smith, III, Merion, PA (US); James Soper, Cambridge, MA (US); John Q. Trojanowski, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/489,745

(22) Filed: Jun. 6, 2012

(65) Prior Publication Data
US 2012/0329877 A1 Dec. 27, 2012

Related U.S. Application Data

(60) Provisional application No. 61/493,562, filed on Jun. 6, 2011.

(51) Int. Cl.
*A61K 31/18* (2006.01)

(52) U.S. Cl.
USPC .......................................................... 514/604

(58) Field of Classification Search
USPC .......................................................... 514/604
See application file for complete search history.

(56) References Cited

PUBLICATIONS

Ballatore et al., "Cyclopentane-1,3-dione: A Novel Isostere for the Carboxylic Acid Functional Group. Application to the Design of Potent Thromboxane (A2) Receptor Antagonists", J. Med. Chem., Oct. 2011, 54(19), 6969-6983.
Boothe et al., "Synthesis of Aureomycin Degradation Products. II", Journal of the American Chemical Society, Apr. 1953, 75(7), 1732-1733.
Dickinson et al., "Thromboxane Modulating Agents. 3. 1H-Imidazol-1-ylalkyl- and 3-Pyridinylalkyl-Substituted 3-[2-[(Arylsulfonyl)amino]ethyl]benzenepropanoic Acid Derivatives as Dual Thromboxane Synthase Inhibitor/Thromboxane Receptor Antagonists", J. Med. Chem., Oct. 1997, 40(21), 3442-3452.
Dogne et al., "From the design to the clinical application of thromboxane modulators", Current Pharmaceutical Design, Mar. 2006, 12(8), 903-923.
Dogne et al., "Thromboxane A2 Inhibition: Therapeutic Potential in Bronchial Asthma", Am. J. Respir. Med., Jan. 2002, 1(1), 11-17.
Henry et al., "Mitsunobu reactions of n-alkyl and n-acyl sulfonamides—an efficient route to protected amines", Tetrahedron Letters, 1989, 30(42), 5709-5712.
Hiraga, "Structures of cyclopentanepolyones", Chemical & Pharmaceutical Bulletin, Nov. 1965, 13(11), 1300-1306.
Katrusiak, "Structure of 2-methyl-1, 3-cyclopentanedione", Acta Crystallographica Section C: Crystal Structure Communications, 1989, C45, 1897-1899.
Katrusiak, "Structure of I, 3-cyclopentanedione", Acta Crystallographica Section C: Crystal Structure Communications, 1990, C46, 1289-1293.
Koreeda et al., "Easy generation of the dianions of 3-isobutoxycyclopent-2-en-1-ones and their reactions", Journal of the Chemical Society, Chemical Communications, 1979, Issue 10, 449-450.
Nakahata, "Thromboxane A2: Physiology/pathophysiology, cellular signal transduction and pharmacology", Pharmacol. Therapeut., Apr. 2008, 118(1), 18-35.
Patani et al., "Bioisosterism: A Rational Approach in Drug Design", Chem. Rev., Dec. 1996, 96(8), 3147-3176.
Peters et al., "Noncovalent Interactions between Tetrazole and an N,N'-Diethyl-Substituted Benzamidine", The Journal of Organic Chemistry, May 2001, 66(10), 3291-3298.
Ramachary et al., "Direct amino acid-catalyzed cascade biomimetic reductive alkylations: application to the asymmetric synthesis of Hajos-Parrish ketone analogues", Organic & Biomolecular Chemistry, Nov. 2008, 6(22), 4176-4187.
Shenker et al., "The G protein coupled to the thromboxane A2 receptor in human platelets is a member of the novel Gq family", J. Biol. Chem., May 1991, 266, 9309-9313.
Shineman et al., "Thromboxane receptor activation mediates isoprostane-induced increases in amyloid pathology in Tg2576 mice", The J. of Neuroscience, Apr. 30, 2008, 28(18), 4785-4794.
Suzuki et al., "Prophylactic Effects of the Histamine H1 Receptor Antagonist Epinastine and the Dual Thromboxane A2 Receptor and Chemoattractant Receptor-Homologous Molecule Expressed on Th2 Cells Antagonist Ramatroban on Allergic Rhinitis Model in Mice", Biol. Pharm. Bull., Apr. 2011, 34(4), 507-510.
Tilley et al., "Carboxylic acids and tetrazoles as isosteric replacements for sulfate in cholecystokinin analogs", Journal of Medicinal Chemistry, Mar. 1991, 34(3), 1125-1136.
Tominey et al., "Unusually Weak Binding Interactions in Tetrazole-Amidine Complexes", Organic Letters, Mar. 2006, 8(7), 1279-1282.
Xu et al., "The Thromboxane Receptor Antagonist S18886 Attenuates Renal Oxidant Stress and Proteinuria in Diabetic Apolipoprotein E-Deficient Mice", Diabetes, Jan. 2006, 55(1),110-119.
Yamamoto et al., "Modeling of human thromboxane A2 receptor and analysis of the receptor-ligand interaction", J Med Chem., Apr. 1993, 36(7), 820-825.

*Primary Examiner* — San-Ming Hui
*Assistant Examiner* — Jeanmarie Calvilloy
(74) *Attorney, Agent, or Firm* — Woodcock Washburn, LLP

(57) ABSTRACT

The present invention is directed to carboxylic acid-containing pharmaceutical compounds where the carboxylic acid moieties have been substituted with cycloalkyl-dione derivatives, as well as tautomers and pharmaceutically acceptable salt forms thereof. These bioisosteric replacements improve the compound's ability to effectively cross the blood brain barrier and result in improved pharmacokinetic, toxicological, and/or safety profiles.

28 Claims, No Drawings

CYCLOALKYL-DIONE DERIVATIVES AND METHODS OF THEIR USE

CROSS REFERENCE TO RELATED APPLICATION

This application claims the benefit of U.S. Provisional Application No. 61/493,562, filed Jun. 6, 2011, the entirety of which is incorporated by reference herein.

GOVERNMENT SUPPORT

This work was supported by grant NIH/NIA RO1-AG034140. Pursuant to 35 U.S.C. §202, the government may have rights in any patent issuing from this application.

TECHNICAL FIELD

The invention is directed to compounds that include cycloalkyl-dione derivatives as replacements for carboxylic acid moieties.

BACKGROUND

Many pharmaceutical compounds approved for the treatment of a myriad of diseases and disorders include a carboxylic acid residue. The carboxylic acid functional group is oftentimes directly involved in binding with the biological target, resulting in a beneficial therapeutic effect of the compound. Occasionally, however, the carboxylic acid is also associated with an undesirable pharmacokinetic profile. Such undesirable characteristics may include limited permeability, toxicity, and metabolic instability.

One example of a carboxylic acid-containing pharmaceutical compound is compound 12:

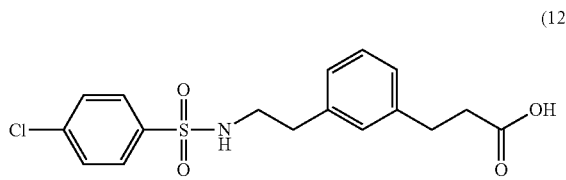

(12)

While compound 12 shows promise as a treatment for Alzheimer's disease, the carboxylic acid moiety impedes the compound's ability to most effectively cross the blood brain barrier. An inability to cross the blood brain barrier inhibits a compound's ability to act on targets within the brain.

As such, bioisosteric replacements for the carboxylic moiety, that is, moieties that mimic the function of the carboxylic acid group but that result in, for example, improved pharmacokinetic, toxicological, and/or safety profiles, especially of compound 12, are needed.

SUMMARY

The present invention is directed to compounds of formula I:

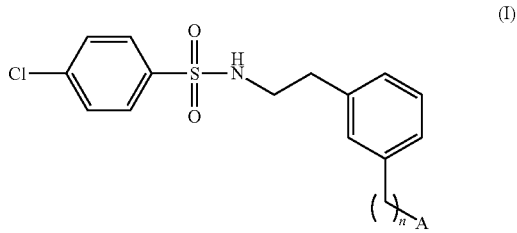

(I)

wherein A is

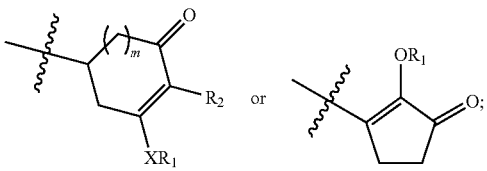

n is 0, 1, or 2; m is 0 or 1; $R_1$ is H or $C_{1-6}$alkyl and $R_2$ is H, $C_{1-6}$alkyl, substituted or unsubstituted aryl, or substituted or unsubstituted heteroaryl; and X is O or N. Tautomers and pharmaceutically acceptable salt forms of compounds of formula I are also within the scope of the invention. Methods of preparing and using the compounds of formula I are also described.

DETAILED DESCRIPTION OF ILLUSTRATIVE EMBODIMENTS

Known thromboxane-A2 prostanoid (TP) receptor antagonist 12 includes a carboxylic acid moiety:

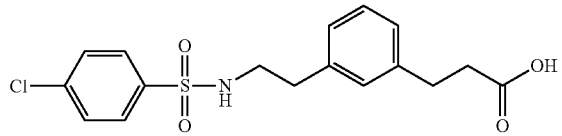

(12)

(Dickinson R. P., et al, "Thromboxane Modulating Agents. 3. 1H-Imidazol-1-ylalkyl- and 3-Pyridinylalkyl-Substituted 3-[2-[(Arylsulfonyl)amino]ethyl]benzenepropanoic Acid Derivatives as Dual Thromboxane Synthase Inhibitor/Thromboxane Receptor Antagonists," J. Med. Chem. 1997, 40(21), 3442-3452, the entirety of which is incorporated by reference). Compound 12 is useful for the treatment of thrombus in patients. In addition, thromboxane receptor antagonists like compound 12 have been shown to be useful in the treatment of Alzheimer's disease. See Shineman, D. W. et al, *Thromboxane Receptor Activation Mediates Isoprostane-Induced Increases in Amyloid Pathology in Tg2576 Mice*, The J. of Neuroscience, Apr. 30, 2008 28(18):4785-4794, the entirety of which is incorporated by reference.

It has now been demonstrated that the carboxylic acid moiety can be replaced by cycloalkyl-1,3-dione and cycloalkyl-1,2-dione derivatives. In particular, it has now been shown that compounds of the invention have commensurate biological activity, as compared to, for example, compound 12. The compounds of the invention will have improved pharmacokinetic profiles as compared to compound 12. It is also within the scope of the invention that compounds of the invention will have other benefits over compound 12, for example, improved therapeutic index, improved efficacy, improved pharmacodynamics, and the like. See Ballatore, C. et al, Cyclopentane-1,3-dione: a novel isostere for the carboxylic acid functional group. Application to the design of potent thromboxane (A2) receptor antagonists, J. Med. Chem. 2011 Oct. 13;54(19):6969-83 incorporated by reference herein.

Within the scope of the invention are compounds of formula I:

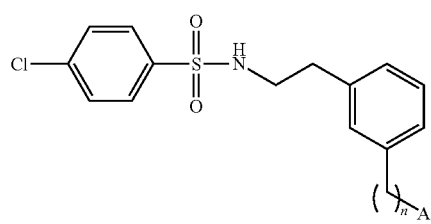

(I)

wherein
A is

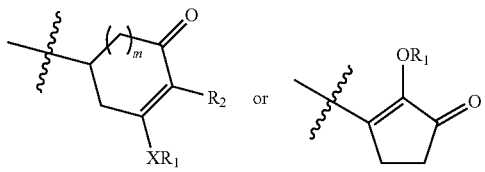

n is 0, 1, or 2;
m is 0 or 1;
$R_1$ is H or $C_{1-6}$alkyl and
$R_2$ is H, $C_{1-6}$alkyl, substituted or unsubstituted aryl, or substituted or unsubstituted heteroaryl; and
X is O or N;
or a tautomer or pharmaceutically acceptable salt form thereof.

In preferred embodiments, A is

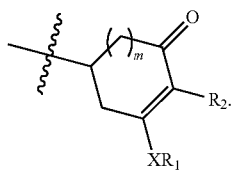

In such embodiments, m is preferably 0. It is also preferred that n is 0 or 1, with n is 1 being most preferred. Particularly preferred embodiments are those wherein m is 0 and n is 1. It is also preferred that $R_1$ is H. It is also preferred that in embodiments employing A, X is O.

In particularly preferred embodiments, A is

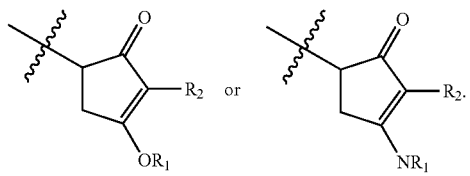

Preferably, $R_2$ is $C_{1-6}$alkyl. Particularly preferred embodiments include those wherein $R_2$ is methyl, ethyl, propyl, isopropyl, —$CH_2$-cyclopropyl, or cyclohexyl. In other embodiments, $R_2$ is H. In still other embodiments, $R_2$ is substituted or unsubstituted aryl, with unsubstituted phenyl being particularly preferred. In yet other embodiments, $R_2$ is substituted or unsubstituted heteroaryl.

In other embodiments wherein A is

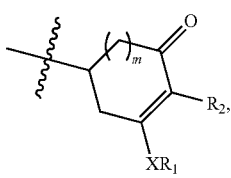

m is 1. It is also preferred, in such embodiments, that n is 0 or 1, preferably 0. Particularly preferred embodiments are those wherein m is 1 and n is 0. It is also preferred that $R_1$ is H. It is also preferred that X is O.

Preferred embodiments include those wherein A is

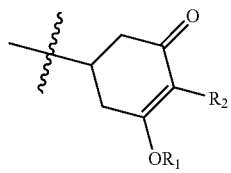

Preferably, $R_2$ is $C_{1-6}$alkyl. Particularly preferred embodiments include those wherein $R_2$ is methyl, ethyl, propyl, isopropyl, —$CH_2$-cyclopropyl, or cyclohexyl. In other embodiments, $R_2$ is H. In still other embodiments, $R_2$ is substituted or unsubstituted aryl, with unsubstituted phenyl being particularly preferred. In yet other embodiments, $R_2$ is substituted or unsubstituted heteroaryl.

Also within the scope of the invention are compounds of formula IA:

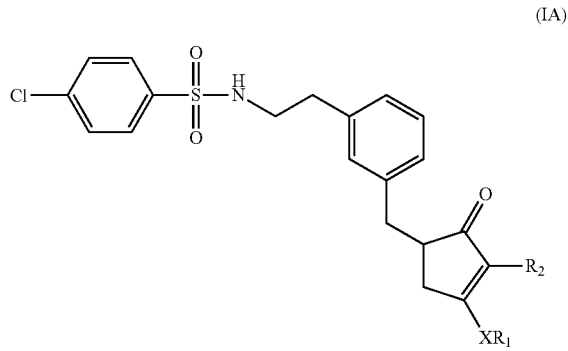

(IA)

wherein $R_1$ is H or $C_{1-6}$alkyl and $R_2$ is H, $C_{1-6}$alkyl, substituted or unsubstituted aryl, or substituted or unsubstituted heteroaryl;

and

X is O or N.

In preferred embodiments, $R_1$ is H. In other embodiments, $R_1$ is $C_{1-6}$alkyl.

In those embodiments wherein $R_1$ is H, $R_2$ is preferably H. In other embodiments wherein $R_1$ is H, $R_2$ is preferably $C_{1-6}$alkyl. In those embodiments, $R_2$ is preferably methyl, ethyl, propyl, or isopropyl. In other embodiments $R_2$ is —$CH_2$-cyclopropyl. In still other embodiments, $R_2$ is substituted or unsubstituted aryl, with unsubstituted phenyl being particularly preferred. In yet other embodiments, $R_2$ is substituted or unsubstituted heteroaryl.

The pharmaceutically acceptable salt forms of compounds of formula I are also within the scope of the invention. Tautomers of compounds of formula I are also within the scope of the invention.

Pharmaceutical formulations can be prepared by combining a compound of the invention with a pharmaceutically acceptable carrier or diluent. Such pharmaceutical formulations can be used to treat thrombus in a patient. Pharmaceutical formulations of the invention can also be used to treat Alzheimer's disease in a patient.

As used herein, "alkyl" refers to branched or unbranched, saturated, hydrocarbons having from 1-30 carbons, preferably 1-6 carbons. Alkyl groups of the invention may also include one or more saturated, cyclic hydrocarbons, for example, cycloalkyl. Preferred alkyl groups include, for example, methyl, ethyl, propyl, isopropyl, butyl, sec-butyl, iso-butyl, tert-butyl, pentyl, isopentyl, and hexyl.

As used herein, "aryl" refers to an aromatic 6-10-membered carbocyclic ring, for example, phenyl and napthyl. Aryl groups used in the compounds of the invention can be unsubstituted. Alternatively, the aryl groups used in the compounds of the invention can be substituted with, for example, halogen (F, Cl, Br, I), alkyl, or alkoxy (—Oalkyl).

As used herein, "heteroaryl" refers to a mono-, di-, or tri-cyclic aromatic ring that includes at least one, preferably 1, 2, 3, or 4, heteroatoms. Heteroatoms include sulfur, oxygen, and nitrogen. Heteroaryl groups also include, for example, from 3 to about 50 carbon atoms, with 4 to 10 carbon atoms being preferred. Examples of heteroaryl groups include pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl groups of the invention can be unsubstituted. Alternatively, heteroaryl groups of the invention can be substituted with, for example, halogen (F, Cl, Br, I), alkyl, or alkoxy (-Oalkyl).

As used herein, "pharmaceutically acceptable salts" refers to those salts of compounds of the invention that are safe and effective for use in a subject and that possess the desired biological activity. Pharmaceutically acceptable salts include salts of acidic or basic groups present in compounds of the invention. Various pharmaceutically acceptable salts, ether derivatives, ester derivatives, acid derivatives, and aqueous solubility altering derivatives of the active compound also are encompassed by the present invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

As used herein, "therapeutically effective amount" refers to an amount effective to ameliorate or prevent the symptoms, prolong the survival of, or otherwise mitigate the undesirable effects of the disease for which the patient is being treated. Determination of a therapeutically effective amount is well within the capabilities of those skilled in the art, especially in light of the detailed disclosure provided herein.

The amount of compound administered will, of course, be dependent on the subject being treated, on the subject's weight, the severity of the affliction, the manner of administration and the judgment of the prescribing physician. However, to the extent that these compounds provide improved activity relative to other known small molecules in in vivo, in vitro, and animal studies, in the broadest sense, recommended dosages are those similar to those currently prescribed for other small molecules for this same purpose.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for oral administration.

To prepare such pharmaceutical dosage forms, one or more of the aforementioned compounds or a pharmaceutically acceptable salt thereof, are intimately admixed with a pharmaceutical carrier according to conventional pharmaceutical compounding techniques. The carrier may take a wide variety of forms depending on the form of preparation desired for administration.

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in a conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For parenteral formulations, the carrier will usually comprise sterile water, though other ingredients, for example, ingredients that aid solubility or for preservation, may be included. Injectable solutions may also be prepared in which case appropriate stabilizing agents may be employed.

Parenteral administration may comprise any suitable form of systemic delivery or delivery directly to the CNS. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In preparing the compositions in oral dosage form, any of the usual pharmaceutical media may be employed. Thus, the compounds can be readily formulated by combining the compounds, salts, or analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

The method for the design and synthesis of model compounds used to evaluate the physical-chemical properties of the compounds of the invention relative to carboxylic acids and tetrazoles is set forth in Scheme 1. Exemplary methods for preparing compounds of the invention are set forth in Schemes 2 and 3.

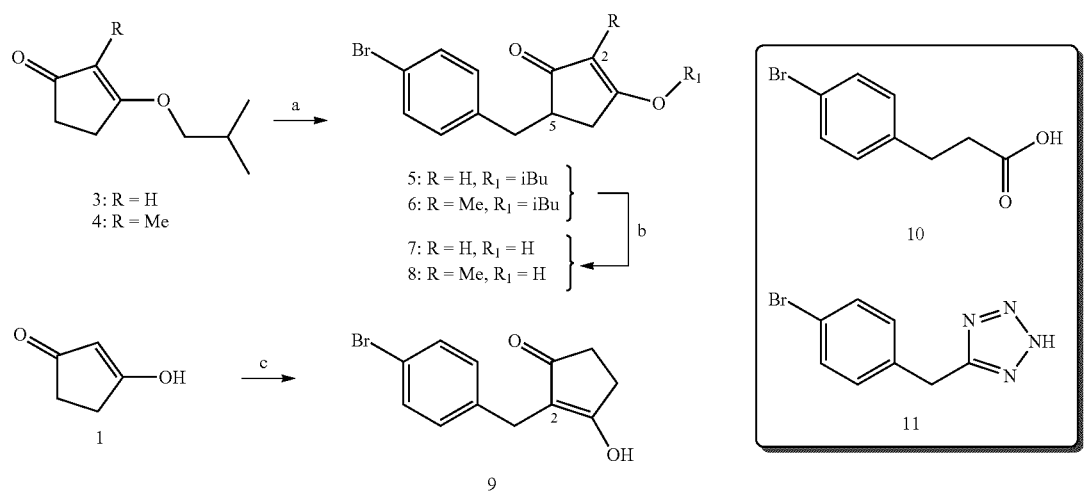
Scheme 1
Reagents and reaction conditions: a) (i) lithium diisopropylamide, -78° C. (ii) 4-bromobenzylbromide, -78° C. to rt over 1 h; b) 2N hydrochloric acid, acetone; c) 4-bromobezaldehyde Hantzsch ester, L-proline, dichloromethane, rt, 2 h.
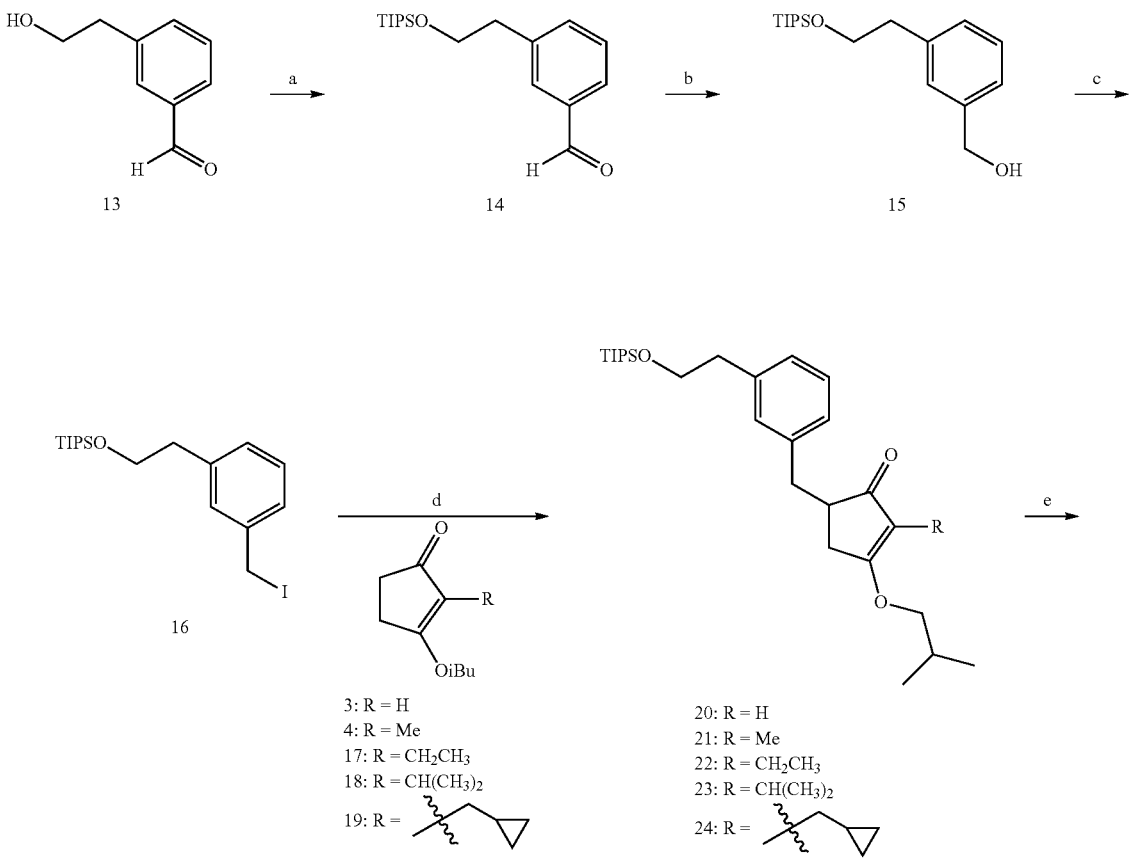
Scheme 2

-continued

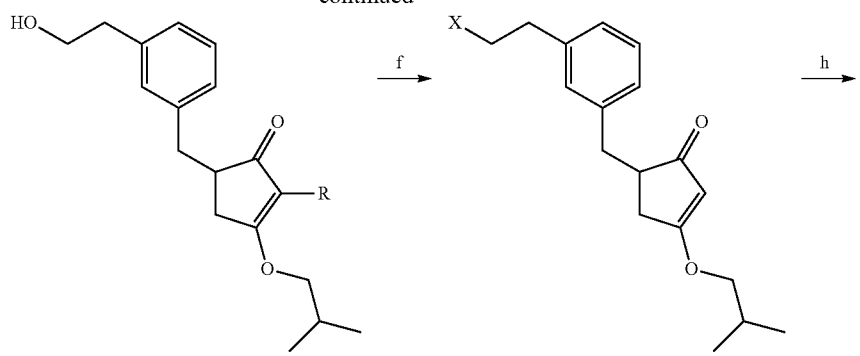

25: R = H
26: R = Me
27: R = CH$_2$CH$_3$
28: R = CH(CH$_3$)$_2$
29: R = 

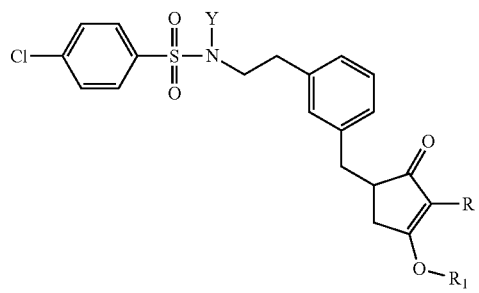

30: X = I
31: X = N$_3$

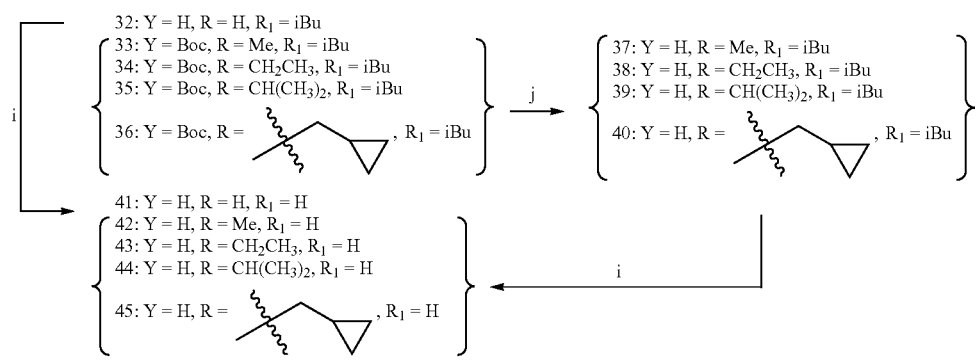

32: Y = H, R = H, R$_1$ = iBu
33: Y = Boc, R = Me, R$_1$ = iBu
34: Y = Boc, R = CH$_2$CH$_3$, R$_1$ = iBu
35: Y = Boc, R = CH(CH$_3$)$_2$, R$_1$ = iBu
36: Y = Boc, R = , R$_1$ = iBu

37: Y = H, R = Me, R$_1$ = iBu
38: Y = H, R = CH$_2$CH$_3$, R$_1$ = iBu
39: Y = H, R = CH(CH$_3$)$_2$, R$_1$ = iBu
40: Y = H, R = , R$_1$ = iBu

41: Y = H, R = H, R$_1$ = H
42: Y = H, R = Me, R$_1$ = H
43: Y = H, R = CH$_2$CH$_3$, R$_1$ = H
44: Y = H, R = CH(CH$_3$)$_2$, R$_1$ = H
45: Y = H, R = , R$_1$ = H

Reagents and reaction condition: a) (i-Pr)$_3$Si—Cl, imidazole, N,N-dimethylformamide, 0° C., 3 h; b) NaBH$_4$, H$_2$O, tetrahydrofuran, 70°C., 2 h; c) PPh$_3$, I$_2$, imidazole, Et$_2$O, acetonitrile, 0° C., 2 h; d) appropriate i-butyl-protected cyclopentane-1,3-dione, lithium diiopropylamide, tetrahydrofuran, from -78° C. to rt; e) tetra-n-butylammonium fluoride, tetrahydrofuran, 0° C., 3 h; f) NaN$_3$, N,N-dimethylformamide, 50° C., 45 min; g) PPh$_3$ diethyl azodicarboxylate, tert-butyl (4-chlorophenyl)sulfonylcarbamate, tetrahydrofuran, rt, 4 h; h) H$_2$, Pd—C, methanol, rt, 16 h, (ii) 4-chlorobenzenesulfonyl chloride, 2N NaOH, 0° C., 3 h; i) 2N HCl, acetone, rt, 6-12 h; j) 2,2,2-trifluoroacetic acid, dichloromethane, rt 2-5 h.

Scheme 3

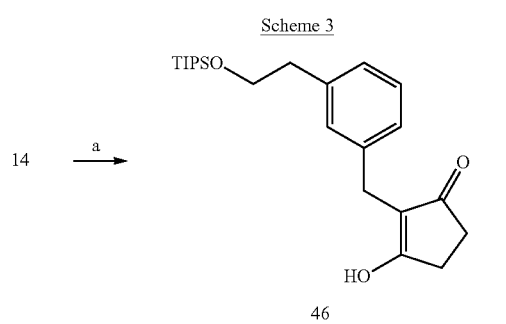
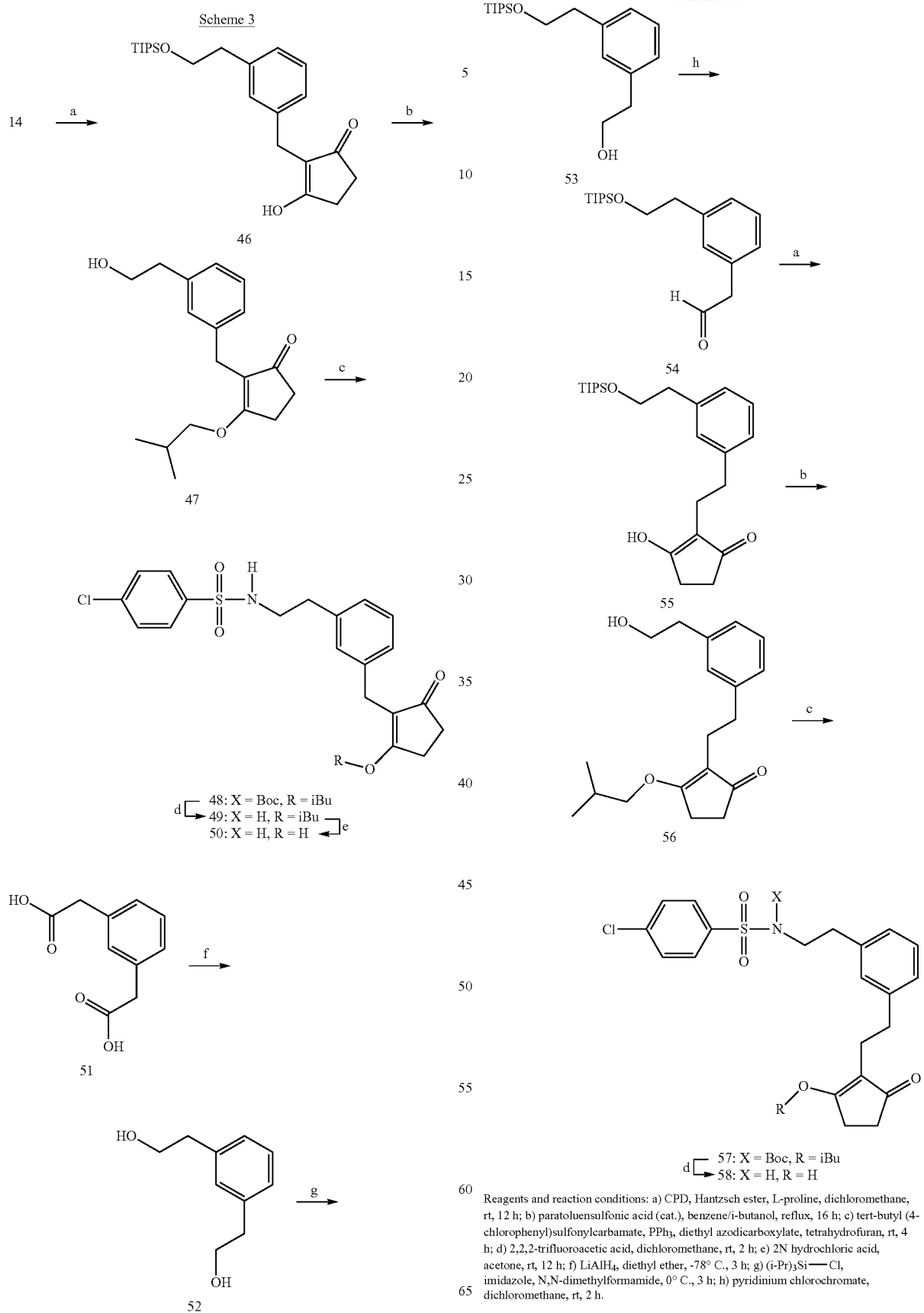

Reagents and reaction conditions: a) CPD, Hantzsch ester, L-proline, dichloromethane, rt, 12 h; b) paratoluensulfonic acid (cat.), benzene/i-butanol, reflux, 16 h; c) tert-butyl (4-chlorophenyl)sulfonylcarbamate, PPh₃, diethyl azodicarboxylate, tetrahydrofuran, rt, 4 h; d) 2,2,2-trifluoroacetic acid, dichloromethane, rt, 2 h; e) 2N hydrochloric acid, acetone, rt, 12 h; f) LiAlH₄, diethyl ether, -78° C., 3 h; g) (i-Pr)₃Si—Cl, imidazole, N,N-dimethylformamide, 0° C., 3 h; h) pyridinium chlorochromate, dichloromethane, rt, 2 h.

Compounds of the invention can also be prepared according to Schemes 4, 5, 6, 7, and 8.
Scheme 4
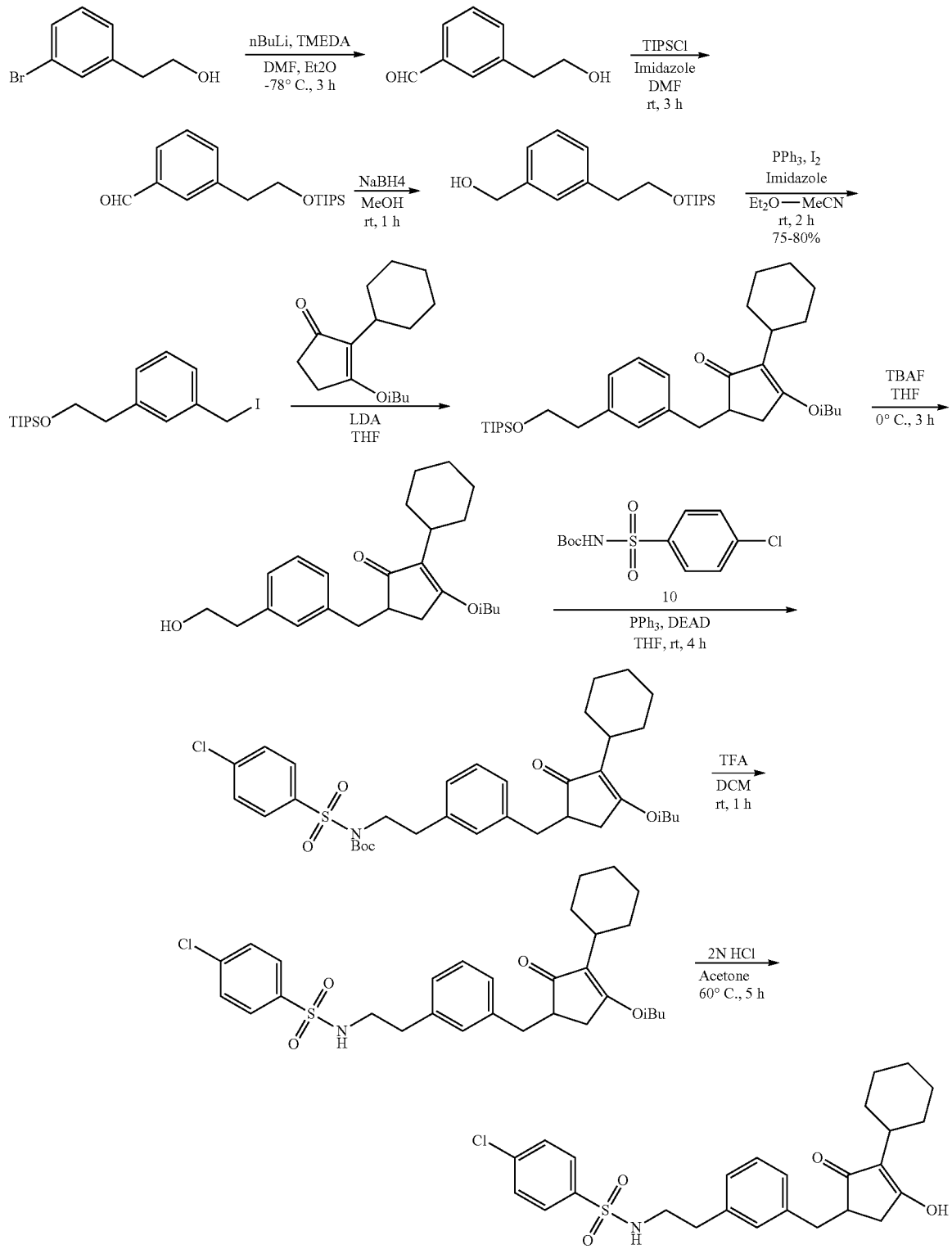

Scheme 5
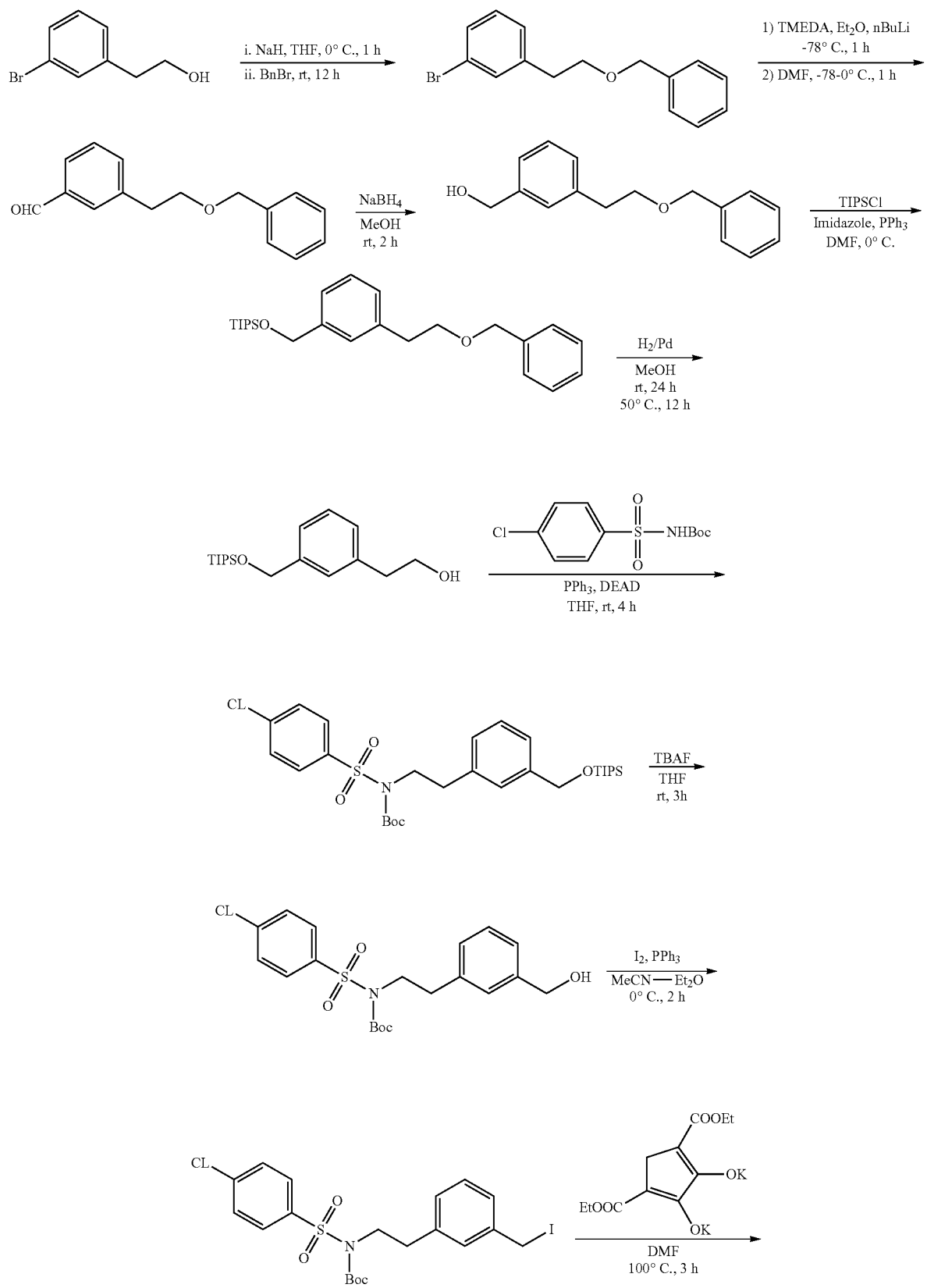

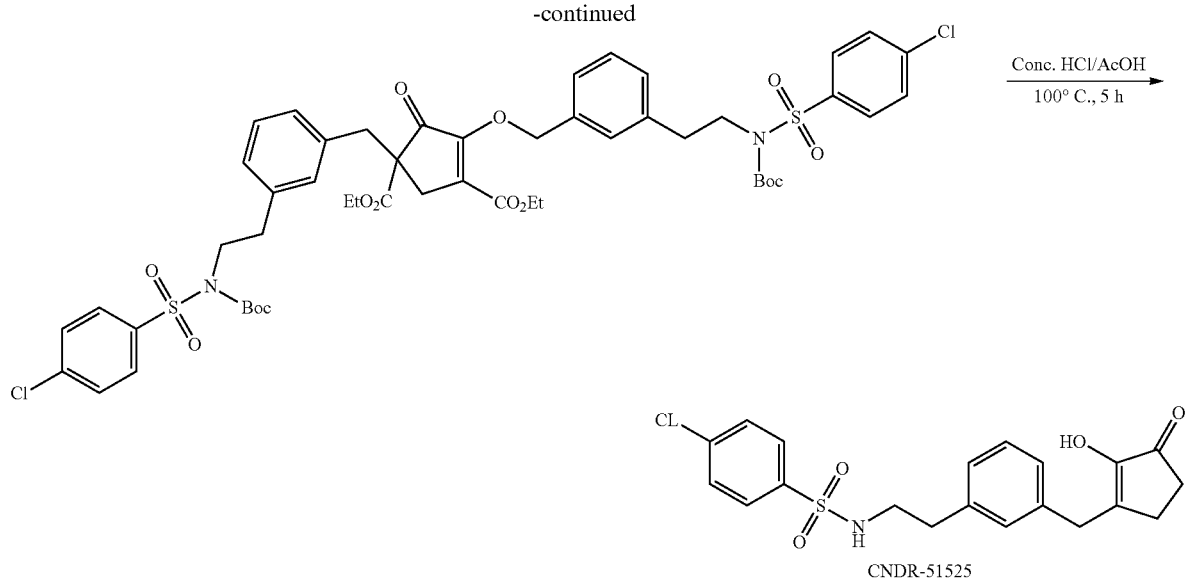
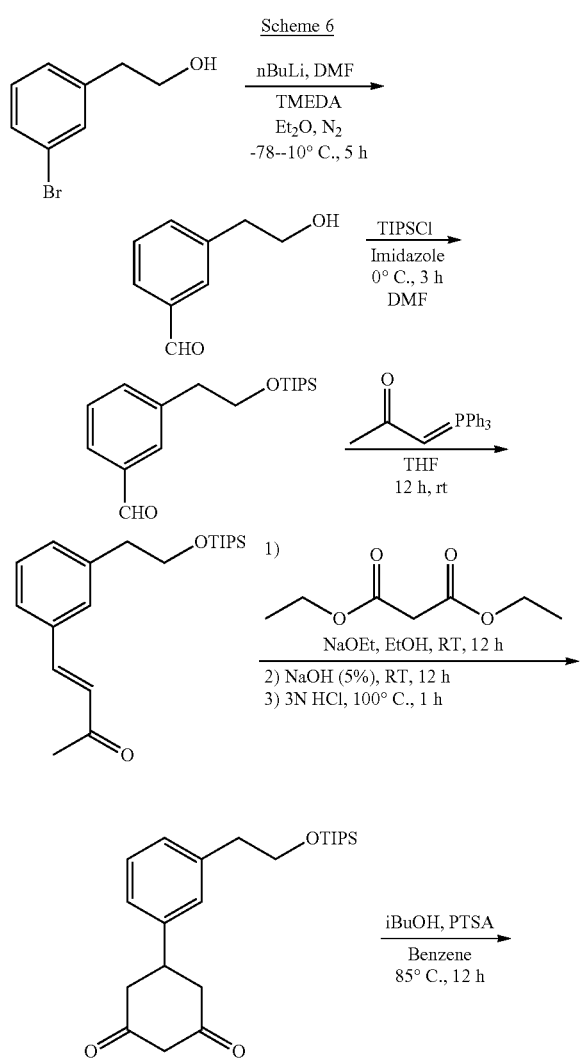
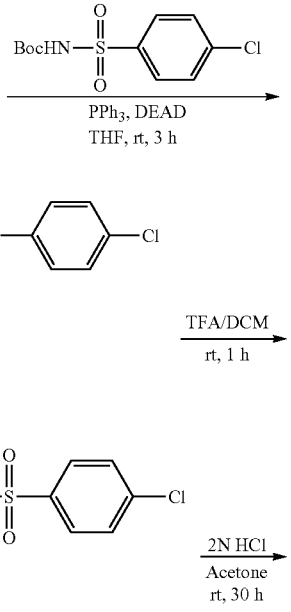

Scheme 7
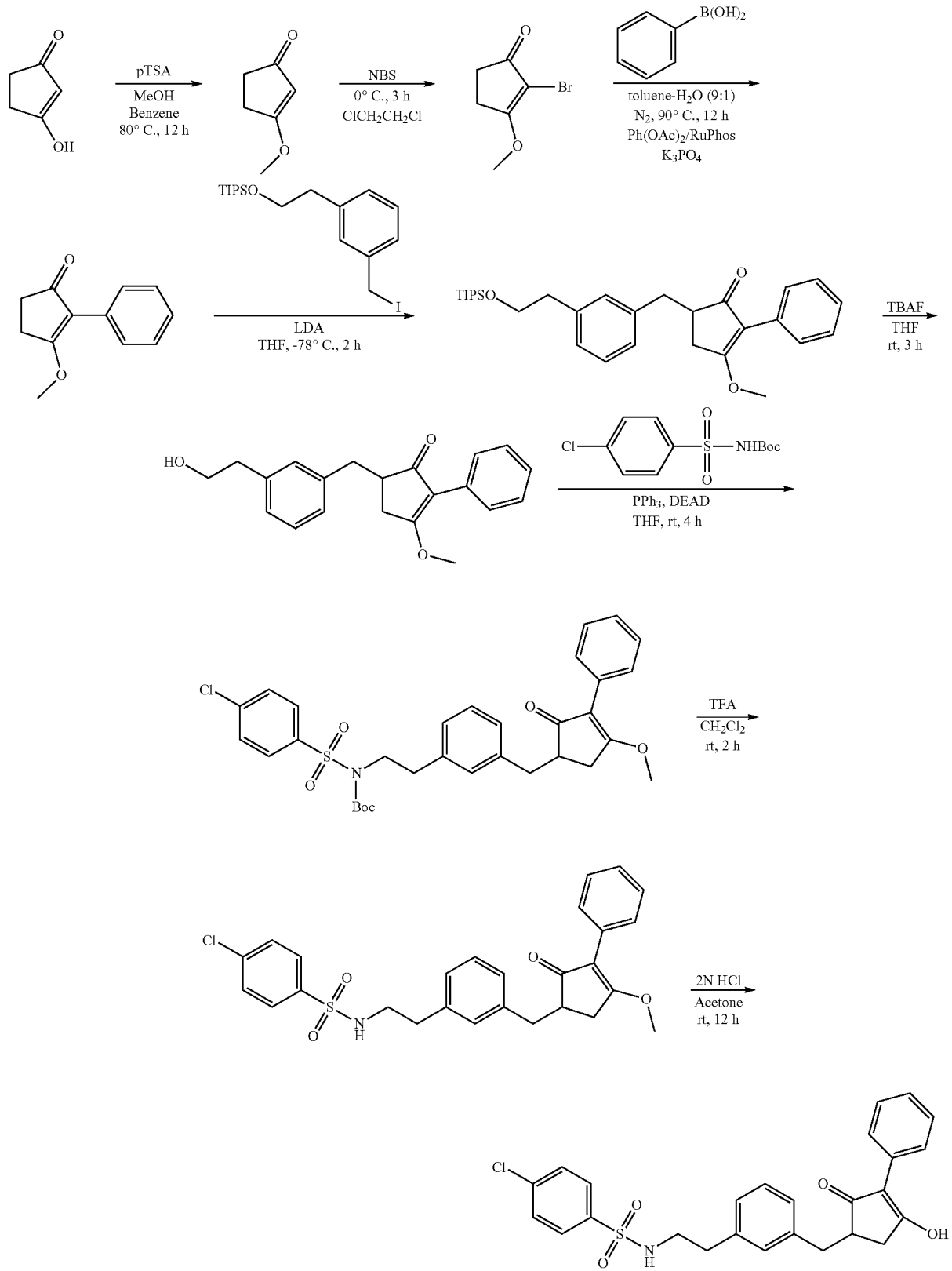

Scheme 8

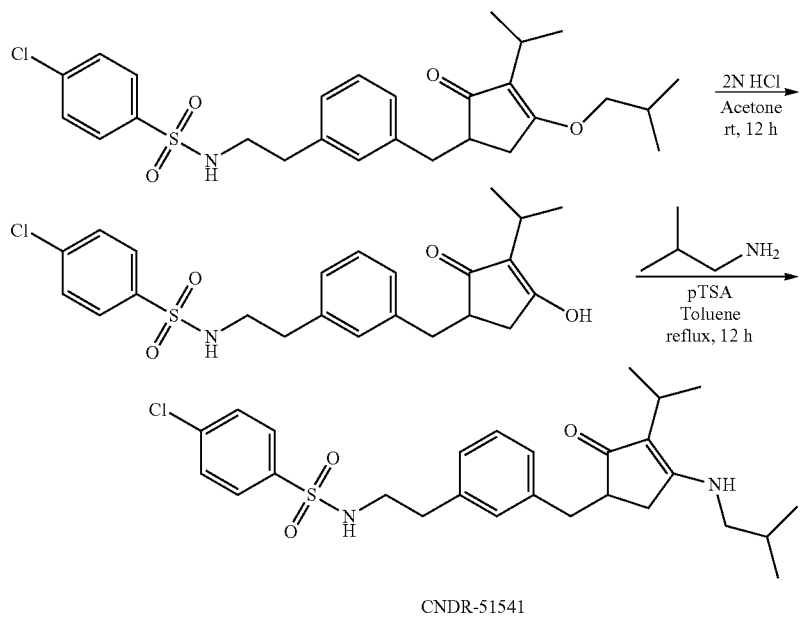

CNDR-51541

It has heretofore been demonstrated that substituting the carboxylic acid moiety with cycloalkyl-dione derivatives provides biologically active compounds that have commensurate biological activity with reference compound 12.

The ability of compounds of the invention to act as antagonists of the human and mouse TP-receptor was determined by a functional IP-One assay and compared with known antagonist 12. Briefly, the IP-One assay depends on a homogeneous time-resolved fluorescence methodology that allows for the measurement of IP1, which is a stable metabolite of the interacellular signal transduction molecule, inositol triphosphate (IP3). It is known that TP receptor activation results in increased release of IP3 (Shenker et al., J. Biol. Chem. 266: 9309-9313; Nakahata, Pharmacol. Therapeut. 118:18-35), and thus an antagonist to this receptor will inhibit agonist-induced increase of IP1 in QB1293 cells that have been stably-transfected with the human or mouse TP receptor. The results are depicted in Tables 1 and 1A.

TABLE 1

|  |  | TP Receptor Antagonist Activity IPOne Assay | |
| --- | --- | --- | --- |
| Cpd # | X | Human TP nM | Mouse TP nM |
| 12 | (CH2CH2COOH) | 61 (+/−21) | 27 (+/−11) |
| 59 | (CH2CH2CH2OH) | 15117 (+/−7994) | 1627 (+/−721) |

TABLE 1-continued

[Structure: 3-substituted phenethyl-N-(4-chlorobenzenesulfonamide) with X-CH2- at meta position]

| Cpd # | X | TP Receptor Antagonist Activity IPOne Assay | |
|---|---|---|---|
| | | Human TP nM | Mouse TP nM |
| 60 | [tetrazole-methyl group] | 64 (+/−41) | 8.0 (+/−6) |
| 61 | [3-hydroxy-4-amino-cyclobutene-1,2-dione] | 377 (+/−203) | 91 (+/−33) |
| 50 | [2-hydroxy-cyclopent-2-enone] | >10,000 | >10,000 |
| 58 | [2-hydroxy-cyclopent-2-enone with methylene linker] | >10,000 | 1229 (+/−462) |
| 41 | [4-hydroxy-cyclopent-3-ene-1,3-dione substituent] | 250 (+/−33) | 52 (+/−17) |
| 42 | [4-hydroxy-3-methyl-cyclopent-3-ene-1,3-dione substituent] | 131 (+/−70) | 3.1 (+/−3.4) |
| 37 | [2-methyl-5-OiBu-cyclopentenone substituent] | >10,000 | 1786 (+/−1212) |

TABLE 1-continued

| Cpd # | X | TP Receptor Antagonist Activity IPOne Assay | |
|---|---|---|---|
| | | Human TP nM | Mouse TP nM |
| 43 | cyclopentenone with OH and ethyl | 171 (+/−35) N = 2 | 9.4 (+/−8.0) N = 2 |
| 38 | cyclopentenone with OiBu and ethyl | 3801 (+/−443) N = 2 | 463 (+/−250) N = 2 |
| 44 | cyclopentenone with OH and isopropyl | 198 (+/−97) | 18 (+/−21) |
| 39 | cyclopentenone with OiBu and isopropyl | 5303 (+/−1078) | 259 (+/−90) |
| 40 | cyclopentenone with OiBu and cyclopropylmethyl | 21853 (+/−2151) | 2524 (+/−233) |
| 45 | cyclopentenone with OH and cyclopropylmethyl | 41 (+/−32) | 5.8 (+/−2.5) |
| 51499 | cyclopentenone with OH and cyclohexyl | 58 nM | 5.6 nM |

TABLE 1-continued

TP Receptor Antagonist Activity
IPOne Assay

| Cpd # | X | Human TP nM | Mouse TP nM |
|---|---|---|---|
| 51525 | (2-hydroxy-5-oxocyclopent-1-en-1-yl) | 50 nM | 20 nM |

TABLE 1A

TP Receptor Antagonist Activity
IPOne Assay

| Cpd # | Human TP nM | Mouse TP nM |
|---|---|---|
| 51523 | 400 nM | 200 nM |

The binding affinity of compounds of the invention against the human and mouse TP-receptor were evaluated via scintillation proximity assay. The results are depicted in Table 2.

TABLE 2

TP Receptor Binding
Scintillation Proximity Assay

| Cpd # | X | Human TP nM | Mouse TP nM |
|---|---|---|---|
| 12 | (carboxymethyl) | 141 (+/−31) | 26 (+/−9.6) |

TABLE 2-continued

[Core structure: phenyl-CH2-X with ethyl-NH-SO2-(4-chlorophenyl) substituent]

| Cpd # | X | TP Receptor Binding Scintillation Proximity Assay | |
|---|---|---|---|
| | | Human TP nM | Mouse TP nM |
| 59 | -CH2CH2OH group | >10,000 | >10,000 |
| 60 | -CH2-tetrazole | 331 (+/−109) | 19 (+/−9.0) |
| 61 | -C(NH)-(3-hydroxy-cyclobutene-dione) | 359 (+/−60) | 17 (+/−7.5) |
| 50 | 2-(3-hydroxy-cyclopent-2-enone)-yl | 11400 (+/−3960) | 1196 (+/−1334) |
| 41 | 4-(2-hydroxy-cyclopent-2-enone)-yl | 203 (+/−87) | 11 (+/−9.5) |
| 42 | 4-(2-hydroxy-3-methyl-cyclopent-2-enone)-yl | 328 (+/−87) | 26 (+/−5.7) |

As those skilled in the art understand, TP-receptor antagonists are useful in treating disease. Ramatroban, a thromboxane A2 receptor antagonist, is marketed in Japan for the treatment of allergic rhinitis. See, e.g., Suzuki, Y., et al., Prophylactic effects of the histamine H1 receptor antagonist epinastine and the dual thromboxane A2 receptor and chemoattractant receptor-homologous molecule expressed on the Th2 cells antagonist Ramatroban on allergic rhinitis model in mice, Biol. Pharm. Bull. 2011; 34(4); 507-10. TP-receptor antagonists have also been reported for the treatment of diabetic complications, including nephropathy (Xu, S. et al., The thromboxane receptor antagonist S18886 attenuates renal oxidant stress and proteinuria in diabetic apolipoprotein E-deficient mice, Diabetes, 2006 January; 55(1):110-9), and bronchial asthma (Dogne J. M., et al. Thromboxane A2 inhibition: therapeutic potential in bronchial asthma, Am. J. Respir. Med. 2002; 1(1):11-17).

EXPERIMENTAL SECTION

Those of skill in the art will readily understand that the following procedures are illustrative only, and are not intended to limit the scope of the invention.

Materials and Methods: All solvents were reagent grade. All reagents were purchased from Aldrich or Acros and used as received. Thin layer chromatography (TLC) was performed with 0.25 mm E. Merck pre-coated silica gel plates. Flash chromatography was performed with silica gel 60 (particle size 0.040-0.062 mm) supplied by Silicycle and Sorbent Technologies. Spots were detected by viewing under a UV light. Yields refer to chromatographically and spectroscopically pure compounds. Infrared spectra were recorded on a Jasco Model FT/IR-480 Plus spectrometer. All melting points were obtained on a Thomas-Hoover apparatus. Proton ($^1$H) and carbon ($^{13}$C) NMR spectra were recorded on a Bruker AMX-500 spectrometer. Chemical shifts were reported relative to solvents ($CDCl_3$ 7.27 ppm; $CD_3OD$ 3.35 ppm; DMSO-$d_6$ 2.5 ppm; acetone-$d_6$ 2.05 ppm). High-resolution mass spectra were measured at the University of Pennsylvania Mass Spectrometry Service on either a VG Micromass 70/70H or VG ZAB-E spectrometer. Single-crystal X-ray structure determinations were performed at the University of Pennsylvania with an Enraf Nonius CAD-4 automated diffractometer. Analytical reversed-phased (Sunfire™ C18; 4.6×50 mm, 5 mL) high-performance liquid chromatography (HPLC) was performed with a Water binary gradient module 2525 equipped with Waters 2996 PDA and Water micromass ZQ. All samples were analyzed employing a linear gradient from 10% to 90% of acetonitrile in water over 8 minutes and flow rate of 1 mL/min, and unless otherwise stated, the purity level was >95%. Preparative reverse phase HPLC purification was performed employing Waters SunFire™ prep $C_{18}$ OBD™ columns (5 μm 19×50 or 19×100 mm). All samples were purified employing a linear gradient from 10% to 90% of acetonitrile in water or 15 minutes and flow rate of 20 mL/min. The preparative HPLC system was equipped with Gilson 333 pumps, a 215 Liquid Handler, 845Z injection module, and PDA detector. Unless otherwise stated, all final compounds were found to be >95% pure as determined by HPLC/MS and NMR.

5-(4-Bromobenzyl)-3-isobutoxycyclopent-2-enone (5). 3-Isobutoxycyclopent-2-enone (3, 0.130 g, 0.84 mmol) in anhydrous tetrahydrofuran (2.0 mL) was cooled to −78° C. and a freshly prepared 1M solution of lithium diisopropylamide (1.0 mL, 1.0 mmol) was added dropwise. The mixture was stirred at −78° C. for 45 min and a solution of 1-bromo-4-(bromomethyl)benzene (0.210 g, 0.84 mmol) in anhydrous tetrahydrofuran (3.0 mL) was added dropwise. The resulting mixture was stirred for 1 h allowing the temperature to rise to rt. The reaction was quenched with a saturated aqueous solution of ammonium chloride (3.0 mL). The aqueous phase was extracted with ethyl acetate (2×10 mL) and combined organic layers were washed with brine, dried over magnesium sulfate, filtered and concentrated in vacuo. Purification by silica gel column chromatography using a gradient of ethyl acetate in hexanes as eluant provided 5 as a white solid (40% yield).

1H NMR (CDCl3): δ 0.94 (d, J=6.7 Hz, 6H), 2.00 (m, 1H), 2.27 (dd, J=17.7, 2.2 Hz, 1H), 2.55-2.61 (m, 2H), 2.71-2.74 (m, 1H), 3.12 (dd, J=14.0, 4.2 Hz, 1H), 3.67 (d, J=6.4 Hz, 2H), 5.20 (s, 1H), 7.04 (d, J=8.3 Hz, 2H), 7.35-7.36 (m, 2H) ppm.

13C NMR (CDCl3): δ 19.05, 19.07, 27.9, 34.1, 36.4, 46.4, 78.1, 104.0, 120.3, 130.8, 131.6, 138.5, 189.2, 206.7 ppm.

IR (film): v 2962, 2931, 2876, 1692, 1593 cm-1.

5-(4-Bromobenzyl)-3-isobutoxy-2-methylcyclopent-2-enone (6). Prepared as 5 from 4. Yield 20%.

1H NMR (CDCl3): δ 0.97 (d, J=6.5 Hz, 6H), 1.65 (s, 3H), 1.65-2.00 (m, 1H), 2.21-2.25 (m, 1H), 2.52-2.57 (m, 1H), 2.60-2.65 (m, 1H), 2.73-2.76 (m, 1H), 3.22 (dd, J=16.5, 4.5 Hz, 1H), 3.83 (dd, J=1.5, 0.5 Hz, 2H), 7.08 (d, J=8.5 Hz, 2H), 7.42 (d, J=8.5 Hz, 2H) ppm.

13C NMR ($CDCl_3$): δ 6.2, 18.9, 28.8, 31.0, 36.7, 45.8, 75.7, 115.4, 120.2, 130.7, 131.6, 138.6, 183.2, 206.1 ppm.

IR (film): v 3384, 3283, 1725 cm-1.

MS (ESI+): calculated for C17H22BrO2+337.08; found 337.01.

5-(4-Bromobenzyl)-3-hydroxycyclopent-2-enone (7). To a mixture of 5 (0.110 g, 0.34 mmol) in acetone (4.2 mL) 2 N hydrochloric acid (1.7 mL) was added at rt and the mixture was stirred for 16 h. The reaction mixture was then concentrated under reduced pressure and the residue is purified by preparative reverse phase HPLC providing 7 as a white solid (46% yield).

mp: 206-208° C. (from methanol)

1H NMR (MeOD): δ 2.20 (dd, J=18.1, 2.5 Hz, 1H), 2.52 (dd, J=18.1, 6.9 Hz, 1H), 2.63 (dd, J=13.8, 9.3 Hz, 1H), 2.93 (m, 1H), 3.08 (dd, J=13.8, 4.3 Hz, 1H), 7.13 (d, J=8.3 Hz, 2H), 7.40 (d, J=8.4 Hz, 2H) ppm.

13C NMR (MeOD): δ 37.47, 37.61, 46.0, 105.9, 121.3, 132.2, 132.6, 139.7, 200.1, 204.9 ppm.

IR (film): v 2920, 2680, 2562, 1713, 1555 cm-1.

HRMS [ESI]−: calculated for C12H10O2Br-264.9864; found 264.9869.

5-(4-Bromobenzyl)-3-hydroxy-2-methylcyclopent-2-enone (8). Prepared as 7 from 6.

Yield 84%.

mp: 180-181° C. (from methanol).

1H NMR ($CD_3OD$): δ 1.55 (s, 3H), 2.16 (d, J=17.5 Hz, 1H), 2.49 (d, J=17.5 Hz, 1H), 2.58 (dd, J=13.5, 8.5 Hz, 1H), 2.84-2.88 (m, 1H), 3.11 (dd, J=14.0, 4.0 Hz, 1H), 7.13 (d, J=8.5 Hz, 2H), 7.40 (d, J=8.5 Hz, 2H) ppm.

13C NMR ($CD_3OD$): δ 36.0, 37.8, 45.2, 114.1, 121.3, 132.2, 132.6, 139.8 ppm.

IR (film): v 2922, 2639, 1570 cm-1.

MS (ESI+): calculated for C13H14BrO2+281.02; found 281.13.

2-(4-Bromobenzyl)-3-hydroxycyclopent-2-enone (9). To a solution of cyclopentane-1,3-dione (0.200 g, 2.0 mmol), diethyl 2,6-dimethyl-1,4-dihydropyridine-3,5-dicarboxylate (0.520 g, 2.0 mmol) and L-proline (0.012 g) in dichloromethane (6.6 mL) 4-bromobenzaldehyde (1.130 g; 6.0 mmol) was added and the resulting mixture was allowed to stir at rt for 30 min. Purification by silica gel column chromatography using a gradient of ethyl acetate in hexanes as eluant provided 9 (75% yield).

mp: 199-201° C. (from methanol).

1H NMR ($CD_3OD$): δ 2.51 (s, 4H), 3.38 (s, 2H), 7.12 (d, J=8.2 Hz, 2H), 7.33 (d, J=8.3 Hz, 2H) ppm.

13C NMR (MeOD): δ 27.2, 31.5, 117.6, 120.5, 131.5, 132.3, 141.0 ppm.

IR (film): v 2911, 2532, 1565 cm-1.

HRMS (ESI−): calculated for C12H10BrO2−264.9864; found 264.9872.

3-(2-Hydroxyethyl)benzaldehyde (13). A mixture 2-(3-bromophenyl)ethanol (1.00 g, 0.67 mL, 4.9 mmol) and N,N,N',N'-tetramethylethylenediamine (1.5 mL) in anhydrous diethyl ether (10 mL) was cooled to −78° C. in a dry-ice acetone bath. n-Butyl lithium (2.4 M solution in hexanes, 4.0 mL, 9.8 mmol) was added dropwise and the resulting mixture was allowed to warm to −20° C. (over 1 h) and then cooled again to −78° C. Anhydrous N,N-dimethylformamide (5 mL) was added and the resulting mixture was allowed to reach room temperature and stirred for an additional 1 h. The reaction mixture was quenched with a saturated solution of ammonium chloride and the aqueous portion was extracted with ethyl acetate. The combined extracts were washed with brine, dried over magnesium sulfate, filtered and evaporated. The residue was purified by silica gel column chromatography using ethyl acetate-hexanes 2:3 as eluent to provide the desired compound as colorless oil. Yield: 88%.

$^1$H NMR (CDCl$_3$): δ 1.69 (broad s, 1H), 2.96 (t, J=6.5 Hz, 2H), 3.91 (t, J=6.5 Hz, 2H), 7.47-7.53 (m. 2H), 7.74-7.76 (m, 2H), 10.00 (s, 1H) ppm.

$^{13}$C NMR (CDCl$_3$): δ 39.0, 63.4, 128.4, 129.4, 130.1, 135.5, 136.9, 140.1, 192.6 ppm.

IR: v 3381, 1696 cm$^{-1}$.

3-(2-((Triisopropylsilyl)oxy)ethyl)benzaldehyde (14). Chlorotriisopropylsilane (0.640 g, 0.71 mL, 3.3 mmol) was added dropwise to a 0° C. cooled solution of 13 (0.450 g, 3.0 mmol) and 1H-imidazole (0.410 g, 6.0 mmol) in anhydrous N,N-dimethylformamide (10 mL). The reaction mixture was stirred at 0° C. for 3 h and then diluted with water. The resulting mixture was extracted with diethyl ether, and the combined organic layers were washed with brine, dried over magnesium sulfate, filtered and evaporated. The residue was purified by silica gel column chromatography using ethyl acetate-hexanes 1:9 as eluent to furnish the desired compound as colorless oil. Yield: 96%.

$^1$H NMR (CDCl$_3$): δ 1.00-1.10 (m, 21H), 2.93 (t, J=6.6 Hz, 2H), 3.93 (t, J=6.6 Hz, 2H), 7.45 (t, J=7.5 Hz, 1H), 7.52 (d, J=7.6 Hz, 1H), 7.73 (d, J=7.5 Hz, 1H), 7.76 (s, 1H), 10.00 (s, 1H) ppm.

$^{13}$C NMR (CDCl$_3$): δ 12.1, 18.1, 39.5, 64.4, 127.9, 129.0, 130.6, 135.7, 136.7, 140.9, 192.7 ppm.

IR: v 1703 cm$^{-1}$.

MS [ESI]$^+$: calculated for C$_{18}$H$_{31}$O$_2$Si$^+$ 307 found 307.

(3-(2-((Triisopropylsilyl)oxy)ethyl)phenyl)methanol (15). Sodium borohydride (0.062 g, 1.63 mmol) was added to a mixture of 14 (0.500 g, 1.63 mmol) in tetrahydrofuran (4 mL) and water (0.25 mL). The reaction mixture was heated to reflux temperature for 2 h. After cooling, water was added and the resulting mixture was extracted with ethyl acetate. The combined organic layers were washed with brine, dried over magnesium sulfate, filtered and evaporated. The residue so obtained was dried under high vacuum to afford the desired compound as colorless oil. Yield: 99%.

$^1$H NMR (CDCl$_3$): δ 0.91-1.17 (m, 21H), 1.62 (broad t, J=5.9 Hz, 1H), 2.88 (t, J=7.1 Hz, 2H), 3.89 (d, J=7.1 Hz, 2H), 4.68 (d, J=5.7 Hz, 2H), 7.17 (d, J=7.4 Hz, 1H), 7.21 (d, J=7.5 Hz, 1H), 7.24 (s, 1H), 7.28 (t, J=7.5 Hz, 1H) ppm.

$^{13}$C NMR (CDCl$_3$): δ 12.2, 18.2, 39.9, 64.9, 65.7, 125.0, 128.1, 128.7, 128.8, 139.9, 141.0 ppm.

IR: v 3325 cm$^{-1}$.

(3-(Iodomethyl)phenethoxy)triisopropylsilane (16). A mixture of 15 (0.500 g, 1.63 mmol), triphenylphosphine (1.280 g, 4.89 mmol), imidazole (0.360 g, 5.22 mmol) and iodine (1.320 g, 5.22 mmol) in diethyl ether (20 mL) and acetonitrile (6.0 mL) was stirred at 0° C. for 2 h. The reaction mixture was diluted with ether, and the resulting mixture was washed with water and a 20 wt % solution of thiosulfate in water, dried over magnesium sulfate, filtered and evaporated. The residue was purified by silica gel column chromatography using ethyl acetate-hexanes 1:9 as eluent to provide the desired compound as colorless oil. Yield: 64%.

$^1$H NMR (CDCl$_3$): δ 1.00-1.11 (m, 21H), 2.83 (t, J=6.9 Hz, 2H), 3.89 (t, J=6.9 Hz, 2H), 4.4 (s, 2H), 7.11 (d, J=6.9 Hz, 1H), 7.20-7.27 (m, 3H) ppm.

$^{13}$C NMR (CDCl$_3$): δ 6.1, 12.2, 18.2, 39.7, 64.7, 126.8, 128.9, 129.0, 129.8, 139.2, 140.3 ppm.

MS [ESI]$^+$: calculated for C$_{18}$H$_{32}$IOSi$^+$ 419, found 419.

3-Isobutoxy-5-(3-(2-((triisopropylsilyl)oxy)ethyl)benzyl)cyclopent-2-enone (20). A solution of diisopropylamine (0.040 g, 0.05 mL, 0.38 mmol) in anhydrous tetrahydrofuran (0.3 mL) was cooled to −78° C. using a dry-acetone bath. n-Butyl lithium (2.3 M solution in hexanes, 0.15 mL, 0.35 mmol) was added dropwise, and the resulting mixture was stirred at −78° C. for 1 h. A solution of 3$^8$ (0.050 g, 0.32 mmol) in anhydrous tetrahydrofuran (2 mL) was added dropwise and the reaction mixture was stirred at −78° C. for 45 minutes. A solution of 16 (0.150 g, 0.35 mmol) in anhydrous tetrahydrofuran (1.5 mL) was added dropwise and the resulting mixture was allowed to reach rt. A saturated solution of ammonium chloride was added and the two layers were separated. The aqueous phase was extracted with ethyl acetate and the combined organic layers were washed with brine, dried over magnesium sulfate, filtered and evaporated. The residue so obtained was purified by silica gel column chromatography using ethyl acetate-hexanes 1:3 as eluent to furnish the desired compound as colorless oil. Yield: 49%.

$^1$H NMR (CDCl$_3$): δ 0.95 (d, J=6.5 Hz, 6H), 1.00-1.10 (m, 21H), 1.20-2.10 (m, 1H), 2.32-2.37 (m, 1H), 2.49-2.61 (m, 2H), 2.76-2.80 (m, 1H), 2.82 (t, J=7.1 Hz, 2H), 3.26 (dd, J=13.9, 4.0 Hz, 1H), 3.71 (d, J=7.1 Hz, 2H), 3.87 (t, J=7.1 Hz, 2H), 5.25 (s, 1H), 7.03-7.07 (m, 3H), 7.19 (t, J=8.1 Hz, 1H) ppm.

$^{13}$C NMR (CDCl$_3$): δ 12.1, 18.1, 19.1, 28.0, 34.5, 37.3, 39.9, 46.9, 65.0, 78.1, 103.8, 126.7, 127.3, 128.5, 129.9, 139.6, 139.7, 189.4, 207.3 ppm.

IR: v 1696, 1595 cm$^{-1}$.

MS [ESI]$^+$: calculated for C$_{27}$H$_{44}$O$_3$NaSi$^+$ 467, found 467.

3-Isobutoxy-2-methyl-5-(3-(2-(triisopropylsilyl)oxy)ethyl)benzyl)cyclopent-2-enone (21). Prepared as 20 from 16 and 4. Yield: 56%.

$^1$H NMR (CDCl$_3$): δ 0.95-1.08 (m, 27H), 1.65 (s, 3H), 1.93-1.99 (m, 1H), 2.25-2.30 (m, 1H), 2.45 (dd, J=14.0, 10.8 Hz, 1H), 2.58-2.63 (m, 1H), 2.76-2.78 (m, 1H), 2.83 (t, J=7.1 Hz, 2H), 3.30 (dd, J=14.1, 3.9 Hz, 1H), 3.82 (d, J=6.6 Hz, 2H), 3.87 (t, J=7.3 Hz, 2H), 7.03-7.08 (m, 3H), 7.20 (t, J=7.5 Hz; 1H) ppm.

$^{13}$C NMR (CDCl$_3$): δ 6.2, 12.1, 18.1, 18.9, 28.8, 31.3, 37.5, 39.8, 46.2, 64.9, 75.6, 115.3, 126.6, 127.3, 128.4, 129.8, 139.6, 139.8, 183.3, 206.6 ppm.

IR: v 1736, 1652, 1634 cm$^{-1}$.

MS [ESI]$^+$: calculated for C$_{28}$H$_{47}$O$_3$Si$^+$ 459.33, found 459.28.

2-Ethyl-3-isobutoxy-5-(3-(2-((triisopropylsilyl)oxy)ethyl)benzyl)cyclopent-2-enone (22). Prepared as 20 from 16 and 17. Yield: 48%.

$^1$H NMR (CDCl$_3$): δ 0.96 (dd, J=6.7, 1.6 Hz, 6H), 0.99-1.07 (m, 24H), 1.97 (dt, J=13.3, 6.7 Hz, 1H), 2.16 (q, J=7.6 Hz, 2H), 2.27 (dt, J=17.5, 1.0 Hz, 1H), 2.48 (dd, J=14.0, 10.7 Hz, 1H), 2.60 (dd, J=17.4, 6.8 Hz, 1H), 2.74-2.77 (m, 1H), 2.83 (t, J=7.2 Hz, 2H), 3.29 (dd, J=14.1, 4.0 Hz, 1H), 3.80 (d, J=6.5 Hz, 2H), 3.86-3.89 (m, 2H), 7.06 (dt, J=12.4, 6.7 Hz, 3H), 7.20 (t, J=7.5 Hz, 1H) ppm.

$^{13}$C NMR (CDCl$_3$): δ 12.2, 12.8, 14.8, 18.2, 19.0, 28.9, 31.0, 37.5, 39.9, 46.2, 65.0, 75.5, 121.4, 126.8, 127.3, 128.5, 129.9, 139.65, 139.80, 183.3, 206.2 ppm.

3-Isobutoxy-2-isopropyl-5-(3-(2-((triisopropylsilyl)oxy)ethyl)benzyl)cyclopent-2-enone (23). Prepared as 20 from 16 and 18. Yield: 68%.

$^1$H NMR (CDCl$_3$): δ 0.96 (dd, J=6.7, 0.9 Hz, 6H), 1.02-1.08 (m, 21H), 1.09-1.14 (m, 6H), 1.96 (dd, J=13.3, 6.6 Hz, 1H), 2.25 (dd, J=17.4, 2.3 Hz, 1H), 2.49 (dd, J=14.0, 10.5 Hz, 1H), 2.58 (dd, J=17.4, 6.9 Hz, 1H), 2.72 (td, J=7.3, 3.3 Hz, 1H), 2.77 (t, J=7.1 Hz, 1H), 2.83 (t, J=7.1 Hz, 2H), 3.25 (dd,

J=14.0, 4.0 Hz, 1H), 3.78 (d, J=6.0 Hz, 2H), 3.87 (t, J=7.2 Hz, 2H), 7.05 (dt, J=13.4, 7.0 Hz, 3H), 7.19 (t, J=7.5 Hz, 1H) ppm.

$^{13}$C NMR (CDCl$_3$): δ 12.2, 18.2, 19.1, 20.5, 23.0, 28.9, 30.7, 37.5, 39.9, 46.0, 65.0, 75.5, 124.8, 126.8, 127.3, 128.4, 129.9, 139.59, 139.72, 183.0, 205.7 ppm.

2-(Cyclopropylmethyl)-3-isobutoxy-5-(3-(2-((triisopropylsilyl)oxy)ethyl)benzyl)cyclopent-2-enone (24). Prepared as 20 from 16 and 19. Yield: 44%.

$^1$H NMR (CDCl$_3$): δ 0.10-0.13 (m, 2H), 0.33-0.36 (m, 2H), 0.87 (m, 1H), 0.95 (dd, J=6.7, 0.6 Hz, 6H), 1.02-1.07 (m, 21H), 1.97 (m, 1H), 2.06 (d, J=6.8 Hz, 2H), 2.27-2.31 (m, 1H), 2.49 (dd, J=14.1, 10.6 Hz, 1H), 2.63 (dd, J=17.4, 6.9 Hz, 1H), 2.78 (m, 1H), 2.82 (t, J=7.1 Hz, 2H), 3.28 (dd, J=14.1, 4.0 Hz, 1H), 3.80 (d, J=6.5 Hz, 2H), 3.86 (t, J=7.2 Hz, 2H), 7.05 (m, 3H), 7.18 (t, J=7.9 Hz, 1H) ppm.

$^{13}$C NMR (CDCl$_3$): δ 4.6, 10.0, 12.1, 18.1, 19.0, 26.0, 28.8, 31.0, 37.4, 39.9, 46.2, 64.9, 75.5, 119.6, 126.7, 127.3, 128.4, 129.8, 139.6, 139.7, 183.6, 206.1 ppm.

5-(3-(2-Hydroxyethyl)benzyl)-3-isobutoxycyclopent-2-enone (25). A solution of tetrabutylammonium fluoride (1 M in tetrahydrofuran, 0.47 mL, 0.47 mmol) was added dropwise to an ice-water bath cooled solution of 20 (0.071 g, 0.16 mmol) in anhydrous tetrahydrofuran (1 mL). The reaction mixture was stirred at 0° C. for 3 h and then quenched with a saturated solution of ammonium chloride. The two phases were separated and the aqueous layer was extracted with diethyl ether. The combined organic layers were washed with brine, dried over magnesium sulfate, filtered and evaporated. The residue was purified by silica gel column chromatography using dichloromethane-methanol 95:5 as eluent to provide the desired product as colorless oil.

Yield: 82%.

$^1$H NMR (CDCl$_3$): δ 0.96 (d, J=6.7 Hz, 6H), 1.98-2.16 (m, 1H), 2.34 (dd, J=17.7, 2.3 Hz, 1H), 2.54-2.63 (m, 2H), 2.75-2.80 (m, 1H), 2.84 (t, J=6.7 Hz, 2H), 3.22 (dd, J=13.9, 4.1 Hz, 2H), 3.70 (d, J=5.8 Hz, 2H), 3.83 (t, J=6.6 Hz, 2H), 5.24 (s, 1H), 7.05-7.08 (m, 3H), 7.21 (t, J=8.1 Hz, 1H) ppm.

$^{13}$C NMR (CDCl$_3$): δ 19.1, 28.0, 34.4, 37.2, 39.3, 46.7, 63.7, 78.2, 103.9, 127.1, 127.2, 128.8, 129.8, 139.0, 139.9, 189.5, 207.5 ppm.

IR: ν 3399, 1685, 1590 cm$^{-1}$.

MS [ESI]$^+$: calculated for C$_{18}$H$_{25}$O$_3^+$ 289.18, found 289.21.

5-(3-(2-hydroxyethyl)benzyl)-3-isobutoxy-2-methylcyclopent-2-enone (26). Prepared as 25 from 21. Yield: 78%.

$^1$H NMR (CDCl$_3$): δ 0.95-0.96 (m, 6H), 1.64 (s, 3H), 1.92-2.00 (m, 2H), 2.28 (d, J=17.4 Hz, 1H), 2.52 (dd, J=14 and 10.4 Hz, 1H), 2.60-2.65 (m, 1H), 2.75-2.80 (m, 1H), 2.85 (t, J=7.5 Hz, 2H), 3.26 (dd, J=14.0 and 4.0 Hz, 1H), 3.80-3.86 (m, 4H), 7.05-7.09 (m, 3H), 7.23 (t, J=7.8 Hz, 1H) ppm.

$^{13}$C NMR (CDCl$_3$): δ 6.2, 19.0, 28.9, 31.3, 37.5, 39.3, 46.1, 63.8, 75.7, 115.4, 127.1, 127.2, 128.8, 129.8, 139.0, 140.1, 183.3, 206.7 ppm.

IR: ν 3404, 1680, 1620 cm$^{-1}$.

MS [ESI]$^+$: calculated for C$_{19}$H$_{27}$O$_3^+$ 303.20, found 303.26.

2-Ethyl-5-(3-(2-hydroxyethyl)benzyl)-3-isobutoxycyclopent-2-enone (27). Prepared as 25 from 22. Yield: 86%.

$^1$H NMR (Acetone-d$_6$): δ 0.93-0.96 (m, 9H), 1.94 (dt, J=13.3, 6.7 Hz, 1H), 2.08 (q, J=7.6 Hz, 2H), 2.42 (dt, J=17.3, 1.1 Hz, 1H), 2.54 (dd, J=13.7, 9.7 Hz, 1H), 2.67 (ddt, J=9.6, 4.4, 2.3 Hz, 1H), 2.72-2.79 (m, 3H), 3.10 (dd, J=13.7, 4.0 Hz, 1H), 3.73 (t, J=7.1 Hz, 2H), 3.92 (dd, J=6.5, 3.1 Hz, 2H), 7.07 (t, J=6.4 Hz, 2H), 7.12 (s, 1H), 7.17 (t, J=7.5 Hz, 1H) ppm.

$^{13}$C NMR (Acetone-d$_6$): δ 13.5, 15.7, 19.5, 29.9, 31.6, 38.1, 40.8, 47.2, 64.4, 76.3, 121.4, 127.9, 128.1, 129.5, 131.0, 140.96, 140.98, 184.4, 205.8 ppm.

5-(3-(2-Hydroxyethyl)benzyl)-3-isobutoxy-2-isopropylcyclopent-2-enone (28). Prepared as 25 from 23. Yield: 90%.

$^1$H NMR (Acetone-d$_6$): δ 1.07 (d, J=6.7 Hz, 6H), 1.22 (t, J=7.6 Hz, 6H), 2.02-2.09 (m, 1H), 2.43-2.48 (m, 1H), 2.69-2.84 (m, 4H), 2.89 (t, J=7.0 Hz, 2H), 3.00 (s, 1H), 3.18 (dd, J=13.1, 3.1 Hz, 1H), 3.83 (t, J=7.0 Hz, 2H), 3.97 (dd, J=6.4, 1.1 Hz, 2H), 7.17-7.21 (m, 3H), 7.33 (t, J=7.5 Hz, 1H) ppm.

$^{13}$C NMR (Acetone-d$_6$): δ 19.7, 21.3, 21.4, 24.3, 30.1, 31.6, 38.3, 40.7, 47.1, 64.5, 76.8, 118.9, 125.2, 128.4, 128.5, 129.8, 131.5, 141.1, 185.2, 206.7 ppm.

2-(Cyclopropylmethyl)-5-(3-(2-hydroxyethyl)benzyl)-3-isobutoxycyclopent-2-enone (29). Prepared as 25 from 24. Yield: 99%.

$^1$H NMR (CDCl$_3$): δ 0.09-0.12 (m, 2H), 0.33-0.37 (m, 2H), 0.87-0.91 (m, 1H), 0.96 (d, J=6.7 Hz, 6H), 1.80 (bs, 1H), 1.97 (dt, J=13.3, 6.7 Hz, 1H), 2.06 (d, J=6.8 Hz, 2H), 2.28-2.32 (m, 1H), 2.55 (dd, J=14.1, 10.3 Hz, 1H), 2.66 (dd, J=17.4, 6.8 Hz, 1H), 2.77-2.81 (m, 1H), 2.85 (t, J=6.6 Hz, 2H), 3.26 (dd, J=14.1, 4.2 Hz, 1H), 3.81 (d, J=6.4 Hz, 2H), 3.85 (t, J=6.6 Hz, 2H), 7.07-7.09 (m, 3H), 7.23 (t, J=7.7 Hz, 1H) ppm.

$^{13}$C NMR (CDCl$_3$): δ 4.6, 10.0, 19.0, 26.0, 28.9, 31.1, 37.4, 39.4, 46.1, 63.8, 75.6, 119.7, 127.2, 128.8, 129.8, 139.0, 140.1, 183.9, 206.3 ppm.

HRMS (ESI$^+$): calculated for C$_{22}$H$_{31}$O$_3^+$ 343.2267, found 343.2268.

5-(3-(2-Iodoethyl)benzyl)-3-isobutoxycyclopent-2-enone (30). Prepared as 16 from 25. Yield: 88%.

$^1$H NMR (CDCl$_3$): δ 0.96 (d, J=6.7 Hz, 6H), 1.99-2.07 (m, 1H), 2.35 (dd, J=17.8, 2.3 Hz, 1H), 2.59-2.63 (m, 2H), 2.77-2.81 (m, 1H), 3.14 (t, J=7.7 Hz, 2H), 3.23 (dd, J=13.9, 4.1 Hz, 1H), 3.35 (t, J=7.3 Hz, 2H), 3.70 (d, J=6.5 Hz, 2H), 5.25 (s, 1H), 7.02-7.04 (m, 2H), 7.10 (d, J=7.6 Hz, 1H), 7.22 (t, J=7.7 Hz, 1H) ppm.

$^{13}$C NMR (CDCl$_3$): δ 6.0, 19.1, 28.0, 34.3, 37.1, 40.3, 46.7, 78.1, 104.0, 126.5, 127.6, 128.9, 129.2, 140.0, 140.9, 189.4, 207.2 ppm.

IR: ν 1691, 1592 cm$^{-1}$.

MS [ESI]$^+$: calculated for C$_{18}$H$_{24}$IO$_2^+$ 398.08, found 398.07.

5-(3-(2-Azidoethyl)benzyl)-3-isobutoxycyclopent-2-enone (31). A mixture of 30 (0.044 g, 0.11 mmol) and sodium azide (0.007 g, 0.11 mmol) in dry N,N-dimethylformamide (0.5 mL) was heated to 50° C. for 45 minutes. The reaction mixture was diluted with water and the resulting mixture extracted with ethyl acetate. The combined organic layers were washed with brine, dried over magnesium sulfate, filtered and evaporated. The residue so obtained was dried under high vacuum to furnish the desired compound. Yield: 76%.

$^1$H NMR (CDCl$_3$): δ 0.97 (d, J=6.7 Hz, 6H), 2.00-2.08 (m, 1H), 2.34 (dd, J=17.8, 2.2 Hz, 1H), 2.57-2.63 (m, 2H), 2.77-2.81 (m, 1H), 2.87 (t, J=7.2 Hz, 2H), 3.24 (dd, J=13.9, 4.1 Hz, 1H), 3.49 (t, J=7.2 Hz, 2H), 3.70 (d, J=6.5 Hz, 2H), 5.25 (s, 1H), 7.06-7.09 (m, 3H), 7.23 (t, J=7.9 Hz, 1H) ppm.

$^{13}$C NMR (CDCl$_3$): δ 19.1, 27.9, 34.3, 35.4, 37.1, 46.7, 52.6, 78.1, 103.9, 126.9, 127.5, 128.9, 129.5, 138.4, 140.1, 189.4, 207.2 ppm.

IR: ν 2097, 1692, 1592 cm$^{-1}$.

MS [ESI]$^+$: calculated for C$_{18}$H$_{24}$N$_3$O$_2^+$ 314.19, found 314.05.

4-Chloro-N-(3-((4-isobutoxy-2-oxocyclopent-3-en-1-yl)methyl)phenethyl)benzenesulfonamide (32). A mixture of 31 (0.059 g, 0.19 mmol) and Pd on C (10 wt %, 0.006 g) in methanol (3 mL) is stirred at rt for 1 h under 1 atmosphere of hydrogen. The reaction mixture was filtered to remove the catalyst. Water (0.5 mL) and 2 N sodium hydroxide (0.27 mL) were added and the reaction mixture was cooled to 0° C. in an ice-water bath. Then 4-chlorophenylsulfonyl chloride (0.082 g, 0.39 mmol) was added and the reaction mixture was stirred at 0° C. for 4 h and then diluted with ethyl acetate. The organic layer was collected, washed with brine, dried over magnesium sulfate, filtered and evaporated. The residue so obtained was purified by silica gel column chromatography, using ethyl acetate-hexanes 1:1 as eluent, to provide the desired compound. Yield: 22%.

$^1$H NMR (CDCl$_3$): δ 0.98 (d, J=6.5 Hz, 6H), 1.99-2.10 (m, 1H), 2.32 (dd, J=17.5, 2.7 Hz, 1H), 2.61-2.65 (m, 2H), 2.75 (t, J=6.6 Hz, 2H), 3.15 (dd, J=13.9, 4.5 Hz, 1H), 3.22-3.26 (m, 2H), 3.71-3.73 (m, 3H), 4.47 (broad t, J=6.2 Hz, 1H), 5.26 (s, 1H), 6.92-6.94 (m, 2H), 7.08 (d, J=7.6 Hz, 1H), 7.21 (t, J=7.8 Hz, 1H), 7.47 (d, J=8.6 Hz, 2H), 7.75 (d, J=8.6 Hz, 2H) ppm.

MS [ESI]$^+$: calculated for C$_{24}$H$_{29}$ClNO$_4$S$^+$ 462.15, found 462.21.

tert-Butyl (4-chlorophenyl)sulfonyl(3-((2-isobutoxy-3-methyl-4-oxocyclopent-2-en-1-yl)methyl)-phenethyl)carbamate (33). Diethyl diazodicarboxylate (40 wt % in toluene, 0.08 mL, 0.28 mmol) was added dropwise to a 0° C. cooled solution of 26 (0.021 g, 0.07 mmol), N-boc-4-chlorobenzenesolfonamide (0.032 g, 0.11 mmol), and triphenylphosphine (0.058 g, 0.22 mmol) in anhydrous tetrahydrofuran (3 mL) under Ar atmosphere. The reaction mixture was stirred at rt for 4 h. Then water was added and the resulting mixture was extracted with diethyl ether. The combined organic layers were washed with brine, dried over magnesium sulfate, filtered and evaporated. The residue was purified by silica gel column chromatography using ethyl acetate-hexanes 1:3 as eluent to furnish the desired compound. Yield: 96%.

$^1$H NMR (CDCl$_3$): δ 0.94 (d, J=6.8 Hz, 6H), 1.34 (s, 9H), 1.65 (s, 3H), 1.91-1.99 (m, 1H), 2.29 (d, J=17.5 Hz, 1H), 2.45-2.49 (m, 1H), 2.60 (dd, J=17.5, 6.7 Hz, 1H), 2.26-2.28 (m, 1H), 3.03 (t, J=7.4 Hz, 2H), 3.31 (dd, J=14.0, 3.4 Hz, 1H), 3.79-3.84 (m, 2H), 4.04 (t, J=5.85 Hz, 2H), 7.09-7.12 (m, 3H), 7.24 (t, J=7.5 Hz, 1H), 7.43 (d, J=8.3 Hz, 2H), 7.69 (d, J=8.3 Hz, 2H) Ppm.

$^{13}$C NMR (CDCl$_3$): δ 6.2, 19.0, 28.1, 28.9, 31.4, 36.6, 37.5, 46.2, 48.6, 75.7, 84.8, 115.3, 127.4, 129.0, 129.1, 129.6, 129.9, 138.4, 138.9, 139.9, 140.5, 150.8, 183.5, 206.5 ppm.

IR: v 1729, 1688, 1631 cm$^{-1}$.

MS [ESI]$^+$: calculated for C$_{30}$H$_{39}$ClNO$_6$S$^+$ 576.22, found 576.06.

tert-Butyl (4-chlorophenyl)sulfonyl(3-((3-ethyl-4:isobutoxy-2-oxocyclopent-3-en-1-yl)methyl)phenethyl)carbamate (34). Prepared as 33 from 27.

Yield: 100%.

$^1$H NMR (Acetone d$_6$): δ 1.00 (dd, J=6.7, 1.3 Hz, 6H), 1.04 (t, J=7.5 Hz, 3H), 1.39 (s, 9H), 1.99 (dt, J=13.4, 6.7 Hz, 1H), 2.16 (q, J=7.5 Hz, 2H), 2.43-2.39 (m, 1H), 2.63 (dd, J=13.8, 9.7 Hz, 1H), 2.72 (dd, J=17.3, 6.8 Hz, 1H), 2.77 (m, 1H), 3.07 (t, J=7.3 Hz, 2H), 3.18 (dd, J=13.8, 4.0 Hz, 1H), 3.93 (d, J=6.6 Hz, 2H), 4.12 (t, J=7.3 Hz, 2H), 7.19 (m, 3H), 7.32 (t, J=7.5 Hz, 1H), 7.63 (d, J=8.6 Hz, 2H), 7.82 (d, J=8.6 Hz, 2H) ppm.

tert-Butyl (4-chlorophenyl)sulfonyl(3-((4-isobutoxy-3-isopropyl-2-oxocyclopent-3-en-1-yl)methyl)phenethyl)carbamate (35). Prepared as 33 from 28.

Yield: 80%.

$^1$H NMR (CD$_3$OD): δ 0.98 (d, J=6.7 Hz, 6H), 1.15 (dd, J=10.3, 7.1 Hz, 6H), 1.30-1.42 (m, 9H), 1.96 (dt, J=13.3, 6.6 Hz, 1H), 2.42 (d, J=15.9 Hz, 1H), 2.63 (dd, J=13.7, 9.1 Hz, 1H), 2.71-2.78 (m, 3H), 3.03 (t, J=7.1 Hz, 2H), 3.16 (dd, J=13.7, 3.8 Hz, 1H), 3.92 (d, J=6.3 Hz, 2H), 4.12 (t, J=7.1 Hz, 2H), 7.14 (m, 3H), 7.26 (d, J=7.4 Hz, 1H), 7.59 (d, J=8.7 Hz, 2H), 7.78 (d, J=8.7 Hz, 2H) ppm.

$^{13}$C NMR (CD$_3$OD): δ 19.3, 20.85, 20.88, 24.1, 28.3, 30.0, 31.7, 37.4, 38.0, 47.0, 77.1, 85.7, 125.3, 128.63, 128.67, 129.9, 130.3, 131.0, 131.3, 139.8, 140.4, 140.85, 140.94, 152.2, 187.4, 208.8 ppm.

tert-Butyl (4-chlorophenyl)sulfonyl(3-((3-(cyclopropylmethyl)-4-isobutoxy-2-oxocyclopent-3-en-1-yl)methyl)phenethyl)carbamate (36). Prepared as 33 from 29.

Yield: 78%.

$^1$H NMR (CDCl$_3$): δ 0.09-0.12 (m, 2H), 0.33-0.36 (m, 2H), 0.87-0.90 (m, 1H), 0.93 (dd, J=6.7, 1.8 Hz, 6H), 1.33 (s, 9H), 1.95 (dt, J=13.3, 6.7 Hz, 1H), 2.06 (d, J=6.8 Hz, 2H), 2.31 (dd, J=17.6, 1.9 Hz, 1H), 2.51 (dd, J=14.1, 10.7 Hz, 1H), 2.63 (dd, J=17.6, 6.8 Hz, 1H), 2.78-2.82 (m, 1H), 3.02 (t, J=7.5 Hz, 2H), 3.30 (dd, J=14.1, 4.0 Hz, 1H), 3.80 (dd, J=6.5, 3.3 Hz, 2H), 4.03 (t, J=7.5 Hz, 2H), 7.10 (q, J=8.8 Hz, 3H), 7.23 (t, J=7.8 Hz, 1H), 7.43 (d, J=8.7 Hz, 2H), 7.69 (d, J=8.7 Hz, 2H) ppm.

4-Chloro-N-(3-((2-hydroxy-4-oxocyclopent-2-en-1-yl)methyl)phenethyl)benzenesulfonamide (41). A mixture of 32 (0.018 g, 0.04 mmol) in acetone (0.5 mL) and 2 N hydrochloric acid (0.2 mL) was stirred at rt for 6 h. The reaction mixture was diluted with water and the acetone was evaporated under reduced pressure. The aqueous phase was extracted with ethyl acetate and the combined organic layers were washed with brine, dried over magnesium sulfate, filtered and evaporated. The residue was purified by reverse phase preparative HPLC to provide the desired compound as a white solid. Yield: 88%.

$^1$H NMR (DMSO-d$_6$): δ 2.05-2.09 (m, 1H), 2.37-2.39 (m, 1H), 2.46 (dd, J=13.7, 10.2 Hz, 1H), 2.64 (t, J=7.3 Hz, 2H), 2.74-2.78 (m, 1H), 2.95-3.01 (m, 3H), 5.06 (s, 1H), 6.97 (d, J=7.6 Hz, 1H), 6.99 (s, 1H), 7.04 (d, J=7.6 Hz, 1H), 7.16 (t, J=7.5 Hz, 1H), 7.64 (d, J=8.6 Hz, 2H), 7.76 (d, J=8.6 Hz, 2H), 7.82 (t, J=5.7 Hz, 1H) ppm.

$^{13}$C NMR (DMSO-d$_6$): δ 22.1, 29.0, 35.2, 36.7, 44.0, 104.5, 126.5, 126.8, 128.3, 128.4, 129.1, 129.6, 137.2, 138.5, 139.4, 139.6 ppm.

IR: v 3402, 1730, 1647, 1580 cm$^{-1}$.

HRMS [ESI]$^+$: calculated for C$_{20}$H$_{20}$ClNNaO$_4$S$^+$ 428.0699, found 428.0714.

4-Chloro-N-(3-((4-isobutoxy-3-methyl-2-oxocyclopent-3-en-1-yl)methyl)phenethyl)benzenesulfonamide (37).

A solution of 33 (0.100 g, 0.173 mmol) in dichloromethane (5 mL) was added with 2,2,2-trifluoroacetic acid (1.5 mL). The resulting mixture was stirred for 1 h at rt. After evaporation of the volatiles, the residue so obtained was purified by preparative reverse phase HPLC to obtain 37. Yield: 73%.

$^1$H NMR (CDCl$_3$): δ 0.97 (dd, J=6.7, 1.3 Hz, 6H), 1.65 (t, J=1.6 Hz, 3H), 1.98 (dt, J=13.4, 6.7 Hz, 1H), 2.28 (dt, J=17.4, 1.9 Hz, 1H), 2.53 (dd, J=14.0, 10.2 Hz, 1H), 2.65 (ddd, J=17.4, 6.8, 1.6 Hz, 1H), 2.75-2.79 (m, 3H), 3.21-3.26 (m, 3H), 3.85 (d, J=6.6 Hz, 2H), 4.45 (t, J=6.2 Hz, 1H), 6.95 (d, J=8.7 Hz, 2H), 7.09 (d, J=7.6 Hz, 1H), 7.22 (t, J=7.4 Hz, 1H), 7.48 (d, J=8.7 Hz, 2H), 7.75 (d, J=8.7 Hz, 2H) ppm.

$^{13}$C NMR (CDCl$_3$): δ 5.3, 18.3, 28.4, 30.9, 35.7, 36.9, 44.1, 45.7, 75.7, 114.9, 126.65, 126.85, 128.04, 128.13, 128.5, 129.09, 138.3, 138.59, 138.72, 139.2, 185.5, 208.1 ppm.

IR: v 2926, 1679, 1618 cm$^{-1}$.

HRMS [ESI]$^+$: calculated for C$_{25}$H$_{31}$ClNO$_4$S$^+$ 476.1662, found 476.1656.

4-Chloro-N-(3-((3-ethyl-4-isobutoxy-2-oxocyclopent-3-en-1-yl)methyl)phenethyl)-benzenesulfonamide (38). A solution of 34 (0.122 g, 0.207 mmol) in dichloromethane (5 mL) and 2,2,2-trifluoroacetic acid (3 mL) was stirred at room temperature for 5 h. The solvent was evaporated and the residue purified by reverse phase preparative HPLC to give the desired product as a colorless oil.

Yield: 80%.

¹H NMR (CDCl₃): δ 0.95 (d, J=6.7 Hz, 6H), 0.98 (t, J=7.5 Hz, 3H), 1.96 (dt, J=13.3, 6.7 Hz, 1H), 2.14 (q, J=7.5 Hz, 2H), 2.26 (dd, J=17.4, 0.9 Hz, 1H), 2.53 (dd, J=14.0, 10.0 Hz, 1H), 2.64 (dd, J=17.4, 6.8 Hz, 1H), 2.71-2.78 (m, 3H), 3.17-3.24 (m, 3H), 3.82 (d, J=6.5 Hz, 2H), 4.87 (t, J=6.1 Hz, 1H), 6.94-6.96 (m, 2H), 7.06 (d, J=7.5 Hz, 1H), 7.18 (d, J=7.5 Hz, 1H), 7.46 (d, J=8.6 Hz, 2H), 7.74 (d, J=8.6 Hz, 2H) ppm.

¹³C NMR (CDCl₃): δ 12.8, 14.8, 19.0, 28.9, 31.1, 36.0, 37.4, 44.4, 46.0, 75.7, 121.4, 126.9, 127.6, 128.7, 129.0, 129.56, 129.62, 138.0, 138.8, 139.2, 140.4, 183.5, 206.1 ppm.

IR: ν 2960, 2920, 2852, 1613 cm⁻¹.

HRMS [ESI]⁺: calculated for $C_{26}H_{32}NO_4NaSI^+$ 512.1638, found 512.1627.

4-Chloro-N-(3-((4-isobutoxy-3-isopropyl-2-oxocyclopent-3-en-1-yl)methyl)phenethyl)benzenesulfonamide (39). Prepared as 38 from 35. Yield: 99%.

¹H NMR (CDCl₃): δ 0.87 (d, J=6.7 Hz, 6H), 1.02 (dd, J=15.4, 7.0 Hz, 6H), 1.85 (m, 1H), 2.29-2.33 (m, 1H), 2.55-2.69 (m, 6H), 2.98 (dd, J=13.4, 3.2 Hz, 1H), 3.05 (t, J=7.2 Hz, 2H), 3.82 (d, J=6.3 Hz, 2H), 6.90-6.93 (m, 2H), 6.97 (d, J=7.6 Hz, 1H), 7.08 (d, J=7.5 Hz, 1H), 7.46 (d, J=8.5 Hz, 2H), 7.71 (d, J=8.5 Hz, 2H) ppm.

¹³C NMR (CDCl₃): δ 19.3, 20.78, 20.81, 24.1, 29.9, 31.4, 37.0, 37.9, 45.6, 46.9, 77.0, 125.4, 128.0, 128.4, 129.64, 129.71, 130.5, 130.8, 139.7, 140.0, 140.4, 140.9, 187.5, 208.9 ppm.

IR: ν 3268, 2963, 2930, 2874, 1671, 1608, 1470, 1383, 1335 cm⁻¹.

HRMS (ESI⁻): calculated for $C_{27}H_{33}ClNO_4S^-$ 502.1819, found 502.1802

4-Chloro-N-(3-((3-(cyclopropylmethyl)-4-isobutoxy-2-oxocyclopent-3-en-1-yl)methyl)phenethyl)benzenesulfonamide (40). Prepared as 37 from 36. Yield: 29%.

¹H NMR (CD₃OD): δ 0.05-0.06 (m, 2H), 0.30-0.32 (m, 2H), 0.84 (m, 1H), 0.98 (d, J=7.0 Hz, 6H), 1.95 (m, 1H), 2.03 (d, J=6.8 Hz, 2H), 2.45 (m, 1H), 2.65-2.69 (m, 1H), 2.74 (t, J=7.2 Hz, 2H), 2.80-2.83 (m, 2H), 3.09-3.15 (m, 3H), 3.95 (dd, J=6.4, 0.7 Hz, 2H), 7.00-7.04 (m, 2H), 7.08 (d, J=7.6 Hz, 1H), 7.19 (t, J=7.6 Hz, 1H), 7.57 (d, J=8.7 Hz, 2H), 7.78-7.80 (m, 2H) ppm.

¹³C NMR (CD₃OD): δ 5.0, 10.8, 19.2, 26.7, 30.0, 31.7, 37.0, 37.9, 45.6, 47.2, 77.2, 120.3, 128.1, 128.4, 129.73, 129.74, 130.5, 130.8, 139.8, 140.2, 140.5, 141.0, 188.4, 209.7 ppm.

HRMS (ESI⁻): calculated for $C_{28}H_{33}ClNO_4S^-$ 514.1819, found 514.1809.

4-Chloro-N-(3-((2-hydroxy-3-methyl-4-oxocyclopent-2-en-1-yl)methyl)phenethyl)-benzenesulfonamide (42). Prepared as 43 from 37. Yield 54%.

¹H NMR (DMSO-d₆): δ 1.43 (s, 3H), 1.98 (d, J=17.4 Hz, 1H), 2.30 (dd, J=17.3, 7.0 Hz, 1H), 2.37 (dd, J=13.5, 10.2 Hz, 1H), 2.62-2.65 (m, 3H), 2.94-2.98 (m, 2H), 3.03 (dd, J=13.5, 3.6 Hz, 1H), 6.94-6.97 (m, 2H), 7.02 (d, J=7.6 Hz, 1H), 7.14 (t, J=7.5 Hz, 1H), 7.64 (d, J=8.6 Hz, 2H), 7.76 (d, J=8.6 Hz, 2H), 7.84 (broad t, J=5.6 Hz, 1H) ppm.

¹³C NMR (DMSO-d₆): δ 5.9, 22.0, 35.3, 37.0, 39.0, 43.6, 44.0, 110.8, 126.4, 126.8, 128.2, 128.4, 129.2, 129.4, 137.2, 138.4, 139.3, 139.9, 212.2, 214.7 ppm.

IR: ν 3279 (broad band), 2925, 1608 cm⁻¹.

HRMS [ESI]⁺: calculated for $C_{21}H_{22}ClNNaO_4S^+$ 442.0856, found 442.0847.

4-Chloro-N-(3-((3-ethyl-4-hydroxy-2-oxocyclopent-3-en-1-yl)methyl)phenethyl)-benzenesulfonamide (43). A mixture of 38 (0.005 g, 0.11 mmol) in acetone (5 mL) was added with 2 N hydrochloric acid (5 mL). The reaction mixture was stirred at rt for 13 h and then concentrated, extracted with ethyl acetate (10 mL×2), and washed with brine (5 mL×2). The organic layer was dried with sodium sulfate anhydrous, filtered and concentrated and the residue so obtained was purified by reverse phase preparative HPLC to give the desired compound.

Yield: 75%

¹H NMR (CD₃OD): δ 0.93-0.96 (m, 3H), 2.05-2.17 (m, 3H), 2.45 (dd, J=17.7, 6.8 Hz, 1H), 2.59 (dd, J=13.7, 9.2 Hz, 1H), 2.69-2.74 (m, 2H), 2.82 (m, 1H), 3.11 (m, 3H), 6.99 (t, J=2.0 Hz, 2H), 7.07 (s, 1H), 7.16 (d, J=7.8 Hz, 1H), 7.57-7.58 (m, 2H), 7.79-7.81 (m, 2H) ppm.

¹³C NMR (CDCl₃): δ 12.8, 14.5, 29.4, 29.9, 32.0, 35.9, 37.8, 44.4, 53.9, 120.1, 127.0, 127.8, 128.7, 129.1, 129.7, 130.1, 137.9, 138.5, 139.5, 139.6 ppm.

IR: ν 3388, 2922, 2354, 1608 cm⁻¹.

HRMS (ESI⁻): calculated for $C_{22}H_{23}NO_4SCl^-$ 432.1036, found 432.1036.

4-Chloro-N-(3-((4-hydroxy-3-isopropyl-2-oxocyclopent-3-en-1-yl)methyl)phenethyl)benzenesulfonamide (44). Prepared as 43 from 39. Yield: 50%.

¹H NMR (CDCl₃): δ 1.10 (d, J=6.9 Hz, 6H), 2.17 (bs, 1H), 2.45 (dd, J=17.4, 5.3 Hz, 1H), 2.59-2.78 (m, 5H), 3.04-3.11 (m, 3H), 6.97 (d, J=9.7 Hz, 2H), 7.03 (d, J=5.9 Hz, 1H), 7.15 (s, 1H), 7.55 (d, J=7.3 Hz, 2H), 7.78 (d, J=7.7 Hz, 2H) ppm.

¹³C NMR (CDCl₃): δ 20.70, 20.72, 24.1, 35.84, 37.2, 38.3, 45.3, 45.7, 123.6, 128.0, 128.5, 129.64, 129.78, 130.5, 130.8, 139.8, 140.1, 140.5, 141.0 ppm.

IR: ν 3268, 2962, 2930, 2873, 1672, 1609 cm⁻¹.

HRMS (ESI⁺): calculated for $C_{23}H_{26}ClNO_4SNa^+$ 470.1169, found 470.1165.

4-Chloro-N-(3-((3-(cyclopropylmethyl)-4-hydroxy-2-oxocyclopent-3-en-1-yl)methyl)phenethyl)benzenesulfonamide (45). Prepared as 43 from 40. Yield 56%.

¹H NMR (MeOD): δ 0.04-0.05 (m, 2H), 0.27-0.30 (m, 2H), 0.81-0.85 (m, 1H), 2.00 (d, J=6.7 Hz, 2H), 2.17 (dd, J=17.8, 1.8 Hz, 1H), 2.46 (d, J=6.8 Hz, 1H), 2.58 (dd, J=13.8, 9.1 Hz, 1H), 2.68 (t, J=7.4 Hz, 2H), 2.80-2.88 (m, 1H), 3.07 (m, 3H), 6.95-6.96 (m, 2H), 7.02 (d, J=7.7 Hz, 1H), 7.14 (t, J=7.8 Hz, 1H), 7.53 (d, J=8.7 Hz, 2H), 7.76 (d, J=8.7 Hz, 2H) ppm.

¹³C NMR (MeOD): δ 4.85, 4.87, 10.9, 26.2, 30.9, 37.2, 38.3, 45.8, 118.4, 128.0, 128.5, 129.72, 129.81, 130.6, 130.8, 139.8, 140.1, 140.6, 141.0 ppm.

IR: ν 3279, 2921, 2852, 1729, 1584 cm⁻¹.

HRMS (ESI⁺): calculated for $C_{24}H_{25}ClNO_4S$ 458.1193, found 458.1190.

3-Hydroxy-2-(3-(2-((triisopropylsilyl)oxy)ethyl)benzyl)cyclopent-2-enone (46). To a solution of 14 (0.920 g, 3.0 mmol), 1,3-cyclopentadione (0.098 g, 1.0 mmol), and L-proline (0.005 mg) in dichloromethane (5 mL), diethyl 2,6-dimethyl-1,4-dihydropyridine-3,5-dicarboxylate (0.253 g, 1.0 mmol) was added, and the resulting mixture was allowed to stir at rt for 12 h. The reaction mixture was directly purified by silica gel column chromatography using a gradient of ethyl acetate in hexanes as eluent, obtaining the title compound. Yield: 76%.

¹H NMR (CD₃OD): δ 1.01-1.04 (m, 21H), 2.47 (s, 4H), 2.75 (t, J=6.8 Hz, 2H), 3.40 (s, 2H), 3.85 (t, J=6.8 Hz, 2H), 6.95-6.97 (m, 1H), 7.03 (d, J=7.6 Hz, 1H), 7.08 (t, J=7.4 Hz, 2H) ppm.

¹³C NMR (CDCl₃): δ 13.3, 18.6, 27.8, 31.5, 40.9, 66.2, 118.4, 127.4, 127.8, 129.1, 130.4, 140.4, 141.5 ppm.

2-(3-(2-Hydroxyethyl)benzyl)-3-isobutoxycyclopent-2-enone (47). A mixture containing 46 (0.294 g, 0.757 mmol), paratoluensolfonic acid (0.005 g), i-butanol (1.0 mL) and benzene (4.0 mL) was heated to reflux for 12 h. The reaction mixture was then concentrated and the residue so obtained was purified by silica gel column chromatography using 5% of methanol in dichloromethane as eluent, obtaining the desired compound. Yield: 81%.

$^1$H NMR (CDCl$_3$): δ 0.96 (d, J=6.7 Hz, 6H), 2.00 (m, 1H), 2.39 (dt, J=5.0, 2.4 Hz, 2H), 2.61 (t, J=4.6 Hz, 3H), 2.77 (t, J=6.9 Hz, 2H), 3.41 (s, 2H), 3.76 (t, J=6.9 Hz, 2H), 3.88 (d, J=6.4 Hz, 2H), 6.97 (d, J=7.3 Hz, 1H), 7.11 (m, 3H) ppm.

$^{13}$C NMR (CDCl$_3$): δ 19.0, 25.2, 27.4, 28.8, 33.6, 39.4, 63.7, 75.7, 119.9, 126.6, 126.7, 128.4, 129.4, 138.7, 140.6, 185.3, 204.5 ppm.

IR: ν 3399, 1685, 1590 cm$^{-1}$.

MS (ESI$^+$): calculated for C$_{18}$H$_{25}$O$_3^+$ 289.18, found 289.16.

tert-Butyl (4-chlorophenyl)sulfonyl(3-((2-isobutoxy-5-oxocyclopent-1-en-1-yl)methyl)phenethyl)carbamate (48). Prepared as 33 from 47. Yield: 92%.

$^1$H NMR (CDCl$_3$): δ 0.99 (d, J=6.7 Hz, 6H), 1.37 (s, 9H), 2.04 (td, J=13.1, 6.4 Hz, 1H), 2.44 (m, 2H), 2.65 (m, 2H), 2.98 (t, J=7.8 Hz, 2H), 3.46 (s, 2H), 3.91 (d, J=6.5 Hz, 2H), 4.00 (dd, J=8.6, 7.0 Hz, 2H), 7.02 (m, 1H), 7.17-7.18 (m, 3H), 7.44 (d, J=8.8 Hz, 2H), 7.69 (d, J=8.7 Hz, 2H) ppm.

$^{13}$C NMR (CDCl$_3$): δ 19.1, 25.3, 27.5, 28.1, 28.9, 33.7, 36.6, 48.6, 75.8, 84.7, 119.9, 126.8, 127.2, 128.7, 129.1, 129.53, 129.63, 138.1, 138.9, 139.8, 140.9, 150.8, 185.2, 204.4 ppm.

MS (ESI$^+$): calculated for C$_{29}$H$_{36}$ClNO$_6$S$^+$ 561.20, found 561.83.

4-Chloro-N-(3-((2-isobutoxy-5-oxoecyclopent-1-en-1-yl)methyl)phenethyl)benzenesulfonamide (49).

A solution of 48 (0.120 g, 0.214 mmol) in dichloromethane (5.0 mL) is added with 2,2,2-trifluoroacetic acid (1.5 mL) and the resulting mixture was stirred at rt for 0.5 h. The solvent was evaporated and the residue purified by reverse phase preparative HPLC to furnish the desired compound as white solid. Yield: 51%.

$^1$H NMR (CDCl$_3$): δ 0.99 (d, J=6.7 Hz, 6H), 2.00-2.06 (m, 1H), 2.45 (m, 2H), 2.66 (m, 2H), 2.71 (t, J=6.8 Hz, 2H), 3.19 (q, J=6.6 Hz, 2H), 3.42 (s, 2H), 3.92 (d, J=6.5 Hz, 2H), 4.71 (t, J=6.1 Hz, 1H), 6.84-6.86 (m, 1H), 7.02 (s, 1H), 7.13 (m, 2H), 7.45 (d, J=8.6 Hz, 2H), 7.71 (d, J=8.6 Hz, 2H) ppm.

$^{13}$C NMR (CDCl$_3$): δ 19.1, 25.3, 27.5, 28.9, 33.7, 35.9, 44.4, 75.8, 119.9, 126.3, 127.4, 128.71, 128.89, 129.3, 129.5, 137.6, 138.8, 139.2, 141.1, 185.2, 204.5 ppm.

IR: ν 3270, 3202, 2962, 2929, 2875, 1678, 1616 cm$^{-1}$.

HRMS (ESI$^-$): calculated for C$_{24}$H$_{27}$ClNO$_4$S$^-$ 460.1349, found 460.1348.

4-Chloro-N-(3-((2-hydroxy-5-oxocyclopent-1-en-1-yl)methyl)phenethyl)benzenesulfonamide (50). Prepared as 43 from 49.

mp: 176-178° C. (from ethyl acetate).

$^1$H NMR (DMSO-d$_6$): δ 2.37 (s, 4H), 2.60 (t, J=7.5 Hz, 2H), 2.91-2.95 (m, 2H), 3.27 (s, 2H), 6.89 (d, J=7.5 Hz, 1H), 6.94-7.01 (m, 2H), 7.09 (t, J=7.5 Hz, 1H), 7.65 (d, J=7.8 Hz, 2H), 7.76 (d, J=8.0 Hz, 2H), 7.82 (broad t, J=5.7 Hz, 1H), 11.9 (broad s, 1H) ppm.

$^{13}$C NMR (DMSO-d$_6$): δ 26.4, 35.3, 44.0, 115.2, 125.7, 126.1, 128.0, 128.4, 128.5, 129.3, 137.1, 138.1, 139.3, 140.7 ppm.

IR: n 3090 (acidic band), 1610 cm$^{-1}$.

HRMS [ESI]$^+$: calculated for C$_{20}$H$_{20}$ClNNaO$_4$S$^+$ 428.0699, found 428.0713.

2,2'-(1,3-Phenylene)diethanol (52). 2,2'-(1,3-Phenylene)diacetic acid (1.000 g, 5.15 mmol), dissolved in anhydrous tetrahydrofuran (15 mL) was cooled at 0° C. in an ice bath and then added with lithium aluminum hydride (0.5860 g, 15.45 mmol). The reaction mixture was stirred at 0° C. for 3 h, and finally quenched by addition of hydrochloric acid (1N) until pH=7. The solution was filtered through filter paper, and extracted with ethyl acetate (15 mL×2). The organic layer was washed with brine (15 mL×2), dried over sodium sulfate, filtered and concentrated to dryness. The residue so obtained was purified by silica gel column chromatography eluting with a gradient of ethyl acetate in hexanes (50%-80%) to furnish the desired product. Yield 61%.

$^1$H NMR (MeOD): δ 2.79 (t, J=7.1 Hz, 4H), 3.74 (t, J=7.1 Hz, 4H), 7.05 (dd, J=7.5, 1.5 Hz, 2H), 7.09 (s, 1H), 7.19 (t, J=7.5 Hz, 1H) ppm.

$^{13}$C NMR (MeOD): δ 40.3, 64.3, 127.9, 129.5, 130.8, 140.4 ppm.

2-(3-(2-((Triisopropylsilyl)oxy)ethyl)phenyl)ethanol (53). 2,2'-(1,3-Phenylene)diethanol (0.430 g, 2.59 mmol) and imidazole (0.176 g, 2.59 mmol) were dissolved in anhydrous N,N-dimethylformamide (15 mL) and cooled to 0° C. in an ice bath. Chlorotriisopropylsilane (0.22 mL) was slowly added and the reaction mixture was kept stirring at 0° C. for 3 h, and then diluted with water (5 mL), extracted with ethyl acetate (15 mL×2), and washed with brine (10 mL×2). The organic layer was dried over anhydrous sodium sulfate, filtered, and evaporated to dryness. The residue so obtained was purified by column chromatography eluting with 1:10 of ethyl acetate-hexanes to give the desired compound as a colorless oil. Yield 35%.

$^1$H NMR (CDCl$_3$): δ 1.04-1.06 (m, 21H), 2.85-2.88 (m, 4H), 3.86 (t, J=6.6 Hz, 2H), 3.90 (t, J=7.1 Hz, 2H), 7.08-7.12 (m, 3H), 7.23-7.27 (m, 1H) ppm.

2-(3-(2-((triisopropylsilyl)oxy)ethyl)phenyl)acetaldehyde (54). A mixture of 53 (0.170 g, 0.527 mmol) in dichloromethane (4 mL) was added with Dess-Martin periodinane (0.270 g, 0.632 mmol) and stirring was maintained for 4 h at rt. The reaction mixture was filtered through a pad of celite and then concentrated to dryness. The residue so obtained was purified by silica gel column chromatography, using gradients of ethyl acetate in hexanes as eluent, to obtain the desired compound. Yield 77%.

$^1$H NMR (CDCl$_3$): δ 1.01-1.11 (m, 21H), 2.87 (t, J=7.0 Hz, 2H), 3.65 (d, J=2.5 Hz, 2H), 3.92 (t, J=7.0 Hz, 2H), 7.08 (d, J=7.5 Hz, 1H), 7.12 (s, 1H), 7.19 (d, J=7.5 Hz, 1H), 7.30 (t, J=7.5 Hz, 1H), 9.74 (t, J=2.5 Hz, 1H) ppm.

$^{13}$C NMR (CDCl$_3$): δ 12.1, 18.1, 39.7, 50.7, 64.8, 127.5, 128.4, 129.0, 130.7, 131.8, 140.5, 199.5 ppm.

3-Hydroxy-2-(3-(2-((triisopropylsilyl)oxy)ethyl)phenethyl)cyclopent-2-enone (55).

Prepared as 46 from 54. Yield: 74%.

$^1$H NMR (CD$_3$OD): δ 0.98 (m, 21H), 2.33 (q, J=7.7 Hz, 2H), 2.40 (d, J=7.4 Hz, 4H), 2.60 (q, J=7.5 Hz, 2H), 2.73 (q, J=6.9 Hz, 2H), 3.82 (q, J=7.0 Hz, 2H), 6.97 (m, 3H), 7.07 (t, J=7.4 Hz, 1H) ppm.

$^{13}$C NMR (CD$_3$OD): δ 13.3, 18.6, 24.2, 31.4, 34.9, 40.9, 66.2, 118.2, 127.3, 127.8, 129.2, 130.5, 140.44, 140.45, 143.3 ppm.

2-(3-(2-Hydroxyethyl)phenethyl)-3-isobutoxycyclopent-2-enone (56). Prepared as 47 from 55. Yield: 24%.

$^1$H NMR (CDCl$_3$): δ 0.98 (d, J=6.5 Hz, 6H), 1.98-2.03 (m, 1H), 2.41-2.47 (m, 4H), 2.60-2.62 (m, 2H), 2.73 (t, J=7.5 Hz, 2H), 2.84 (t, J=6.5 Hz, 2H), 3.84-3.87 (m, 4H), 7.02-7.08 (m, 3H), 7.20 (t, J=7.5 Hz, 1H) ppm.

tert-Butyl (4-chlorophenyl)sulfonyl(3-(2-(2-isobutoxy-5-oxocyclopent-1-en-1-yl)ethyl)phenethyl)carbamate (57). Prepared as 33 from 56. Yield: 43%.

$^1$H NMR (CDCl$_3$): δ 0.98 (d, J=6.5 Hz, 6H), 1.59 (s, 9H), 1.98-2.03 (m, 1H), 2.43-2.45 (m, 4H), 2.62 (t, J=4.5 Hz, 2H), 2.73 (t, J=8.0 Hz, 2H), 2.99-3.03 (m, 2H), 3.83-3.86 (m, 2H), 3.98-4.01 (m, 1H), 4.19-4.24 (m, 1H), 7.05-7.11 (m, 3H), 7.21 (t, J=7.5 Hz, 1H), 7.76 (d, J=8.5 Hz, 2H), 7.77 (d, J=8.5 Hz, 2H) ppm.

$^{13}$C NMR (CDCl$_3$): δ 19.1, 23.5, 25.1, 28.1, 28.9, 29.9, 33.8, 33.9, 36.7, 48.8, 75.6, 84.8, 100.2, 119.9, 126.7, 127.0, 128.7, 129.1, 129.4, 129.7, 138.0, 139.0, 139.9, 142.9, 184.9, 204.9 ppm.

4-Chloro-N-(3-(2-(2-isobutoxy-5-oxocyclopent-1-en-1-yl)ethyl)phenethyl)benzenesulfonamide. Prepared as 42 from 57. Yield 28%

1H NMR (CDCl3): δ 1.00 (d, J=6.7 Hz, 6H), 2.06-1.98 (m, 1H), 2.45-2.39 (m, 4H), 2.61 (m, 2H), 2.69 (t, J=7.7 Hz, 2H), 2.73 (t, J=6.7 Hz, 2H), 3.22 (q, J=6.3 Hz, 2H), 3.88 (d, J=6.5 Hz, 2H), 5.03-5.04 (bs, 1H), 6.86 (d, J=7.5 Hz, 1H), 6.95 (s, 1H), 6.99 (d, J=7.6 Hz, 1H), 7.13 (t, J=7.5 Hz, 1H), 7.44 (d, J=8.6 Hz, 2H), 7.75 (d, J=8.6 Hz, 2H) ppm.

13C NMR (CDCl3): δ 19.1, 23.2, 25.2, 28.9, 33.6, 33.8, 36.0, 44.5, 75.8, 119.8, 126.4, 127.2, 128.67, 128.72, 129.2, 129.5, 137.7, 139.00, 139.08, 142.6, 185.9, 205.5 ppm.

HRMS [ESI]+: calculated for C25H30ClNO4SNa+ 498.1482 found 498.1476.

4-Chloro-N-(3-(2-(2-hydroxy-5-oxocyclopent-1-en-1-yl)ethyl)phenethyl)-benzenesulfonamide (58). Prepared as 43 from 57. Yield 84%.

$^1$H NMR (DMSO-d$_6$): δ 2.26 (dd, J=9.5, 6.8 Hz, 2H), 2.34 (bs, 4H), 2.57 (dd, J=9.4, 6.7 Hz, 2H), 2.66 (t, J=7.5 Hz, 2H), 2.98 (q, J=6.7 Hz, 2H), 6.95 (d, J=6.6 Hz, 2H), 7.02 (d, J=7.6 Hz, 1H), 7.16 (t, J=7.9 Hz, 1H), 7.65-7.67 (m, 2H), 7.77-7.80 (m, 2H), 7.83 (t, J=5.7 Hz, 1H), 11.55 (s, 1H) ppm.

$^{13}$C NMR (DMSO-d$_6$): δ 22.8, 27.0, 33.3, 35.3, 44.1, 115.5, 125.99, 126.09, 128.2, 128.40, 128.51, 129.3, 137.2, 138.3, 139.4, 142.0 ppm.

IR: n 3253, 2924, 1709, 1587 cm$^{-1}$.

HRMS [ESI]$^-$: calculated for C$_{21}$H$_{21}$ClNO$_4$S$^-$ 418.0880, found 418.0878.

4-Chloro-N-(3-((3-cyclohexyl-4-hydroxy-2-oxocyclopent-3-en-1-yl)methyl)phenethyl)benzenesulfonamide (CNDR51499):

$^1$H NMR (CDCl$_3$): δ 1.20-1.23 (m, 2H), 1.46-1.48 (m, 2H), 1.64-1.71 (m, 5H), 2.27 (d, J=17.0 Hz, 1H), 2.35-2.39 (m, 1H), 2.52 (dd, J=7.0 and 18.0 Hz, 1H), 2.59-2.63 (m, 1H), 2.73 (t, J=6.5 Hz, 2H), 2.83 (bs, 1H), 3.10-3.21 (m, 3H), 4.94 (t, J=6.0 Hz, 1H), 6.91 (d, J=7.5 Hz, 1H), 6.95 (s, 1H), 7.03 (d, J=8.0 Hz, 1H), 7.14 (t, J=7.5 Hz, 1H), 7.45 (d, J=8.6 Hz, 2H), 7.72 (d, J=8.5 Hz, 2H) ppm.

$^{13}$C NMR (CDCl$_3$): δ26.2, 27.0, 30.2, 30.2, 33.2, 35.9, 37.8, 44.4, 77.0, 122.7, 126.9, 127.8, 128.6, 129.1, 129.7, 130.1, 137.8, 138.4, 139.5, 139.5 ppm.

IR: ν 3351, 2923, 1604, 1383, 1158, 1086 cm$^{-1}$.

HRMS [ESI]$^+$: calculated for C$_{26}$H$_{30}$ClNO$_4$SNa$^+$ 510.1482, found 510.1485.

4-Chloro-N-(3-((2-hydroxy-3-oxocyclopent-1-en-1-yl)methyl)phenethyl)benzenesulfonamide (CNDR51525).

$^1$H NMR (CDCl$_3$): δ 2.35-2.39 (m, 4H), 2.76 (t, J=7.0 Hz, 2H), 3.23 (quart, J=7.0 Hz, 2H), 3.68 (s, 2H), 4.89 (brs, 1H), 6.31 (brs, NH), 6.97 (d, J=8.5 Hz, 2H), 7.09 (d, J=7.5 Hz, 1H), 7.22 (t, J=7.5 Hz, 1H), 7.45 (d, J=9.5 Hz, 2H), 7.74 (d, J=9.0 Hz, 2H) ppm.

$^{13}$C NMR (CDCl$_3$): δ 25.1, 32.1, 35.0, 35.9, 44.4, 127.2, 127.6, 128.7, 129.3, 129.6, 129.6, 138.7, 139.3, 145.8, 148.9, 203.6 ppm.

4-Chloro-N-(2-(5'-hydroxy-3'-oxo-1',2',3',6'-tetrahydro-[1,1'-biphenyl]-3-yl)ethyl)benzenesulfonamide (CNDR-51523).

$^1$H NMR (DMSO-d$_6$): δ 2.37 (dd, J=3.8 and 16.6 Hz, 2H), 2.50-2.58 (m, 2H), 2.67 (t, J=7.5 Hz, 2H), 3.00 (quart, J=7.0 Hz, 2H), 3.22-3.27 (m, 1H), 5.26 (bs, NH), 7.01 (d, J=7.25 Hz, 1H), 7.11 (s, 1H), 7.16 (d, J=7.7 Hz, 1H), 7.20 (t, J=7.5 Hz, 1H), 7.64 (d, J=8.6 Hz, 2H), 7.76 (d, J=8.6 Hz, 2H), 7.81 (t, J=5.7 Hz, 1H) ppm.

$^{13}$C NMR (DMSO-d$_6$): δ 35.2, 38.6, 43.7, 103.3, 124.6, 127.2, 128.3, 128.3, 129.2, 137.0, 138.6, 139.3, 143.5 ppm. (Carbonyl C not observed).

IR: ν 2925, 1594, 1402, 1326, 1219, 1158, 1090, 829, 743, 622 cm$^{-1}$.

HRMS [ESI]$^+$: calculated for C$_{20}$H$_{21}$ClNO$_4$S$^+$ 406.0880, found 406.0883.

4-Chloro-N-(3-((4-hydroxy-2-oxo-3-phenylcyclopent-3-en-1-yl)methyl)phenethyl)benzenesulfonamide (CNDR-51543).

$^1$H NMR (CD$_3$OD-d$_4$): δ 2.05-2.09 (m, 1H), 2.37-2.39 (m, 1H), 2.46 (dd, J=13.7 and 10.2 Hz, 1H), 2.64 (t, J=7.3 Hz, 2H), 2.74-2.78 (m, 1H), 2.95-3.01 (m, 3H), 5.06 (s, 1H), 6.97 (d, J=7.6 Hz, 1H), 6.99 (s, 1H), 7.04 (d, J=7.6 Hz, 1H), 7.16 (t, J=7.5 Hz, 1H), 7.64 (d, J=8.6 Hz, 2H), 7.76 (d, J=8.6 Hz, 2H), 7.82 (t, J=5.7 Hz, 1H) ppm.

$^{13}$C NMR (CD$_3$OD-d$_4$): δ 35.9, 37.2, 38.4, 45.7, 48.6, 101.5, 117.1, 127.7, 128.1, 128.5, 129.0, 129.3, 129.7, 129.8, 130.5, 130.8, 132.7, 139.8, 140.2, 140.5, 141.0 ppm (carbonyl C not observed).

IR: ν 3424 (broad band), 2922, 1582, 1387, 1157, 1087 cm$^{-1}$.

HRMS [ESI]$^+$: calculated for C$_{26}$H$_{25}$ClNO$_4$S$^+$ 482.1193, found 482.1178.

4-Chloro-N-(3-((4-(isobutylamino)-3-isopropyl-2-oxocyclopent-3-en-1-yl)methyl)phenethyl)benzenesulfonamide (CNDR-51541).

$^1$H NMR (CDCl$_3$): δ 0.97 (d, J=6.5 Hz, 6H), 1.10-1.12 (m, 6H), 1.95-2.00 (m, 1H), 2.24 (d, J=18.0 Hz, 1H), 2.53-2.57 (m, 1H), 2.63 (dd, J=7.0 and 17.5 Hz, 1H), 2.71-2.78 (m, 4H), 3.18-3.26 (m, 3H), 3.81 (d, J=6.5 Hz, 2H), 4.46 (bs, NH), 6.95 (d, J=7.5 Hz, 2H), 7.08 (d, J=7.5 Hz, 1H), 7.21 (t, J=7.5 Hz, 1H), 7.48 (d, J=8.5 Hz, 2H), 7.75 (d, J=8.5 Hz, 2H) ppm.

$^{13}$C NMR (CDCl$_3$): δ 19.0, 20.4, 22.9, 28.8, 29.8, 30.7, 35.9, 37.4, 44.3, 45.8, 75.6, 100.1, 124.9, 126.8, 127.6, 128.6, 129.0, 129.5, 129.6, 137.7, 138.7, 140.4 ppm. (Carbonyl C not observed).

IR: ν 3384 (broad band), 2922, 1606, 1379, 1157, 1158, 1086, 757 cm$^{-1}$.

MS [ESI]$^+$: calculated for C$_{27}$H$_{36}$ClN$_2$O$_3$S$^+$ 504.1, found 504.2.

CPD-benzamidine Salt Detection with ESI-MS. CPD-benzamidine salts were detected using ESI-MS with an Acquity TQMS controlled by MassLynx software (Waters Corporation, Milford, Mass., USA). Source gas flow rates, temperatures and voltages were optimized for the detection of intact salt ions. CPD:benzamidine mixtures (10 μM:10 μM) in acetonitrile were vortexed for five minutes at room temperature and then infused using the detector's syringe pump at 30 μL/min. Mass spectra were acquired in positive ion mode with a 0.5 second scan rate over 30 seconds. Scans one through fifty were combined and analyzed.

CPD-benzamidine Relative Affinity by Competition. Compound number 8 and benzamidine were mixed with a competing acid at equimolar amounts (10 μM:10 μM:10 μM) in acetonitrile. Mixtures were vortexed for ten minutes at room temperature then infused into the MS at 30 μL/min. After stabilization of the infusion flow, mass spectra were acquired in positive ion mode with a 0.2 second scan rate over 30 seconds. Scans one through one hundred were combined and the intensity of the 8-benzamidine salt ion, [8($^{79}$Br).benzamidine+H]$^+$ (m/z 401), was recorded. Affinities between acids and the benzamidine base were determined relative to compound number 8 as the average (N=3) reduction of intensity of the 8-benzamidine salt ion in the presence of a competing acid.

Compound Solubility/Turbidity. Serial dilutions in DMSO were further diluted 100 fold with acetonitrile in a clear, flat bottom, 96 well plate to concentrations of 200, 80, 32, 12.8, 5.1, 2.0 0.82 and 0.33 µM. Solutions were then mixed at room temperature on a plate shaker for two hours. Absorbance at 550, 600, 650 and 700 nm was recorded for triplicate solutions at each concentration using a Spectramax M5 microplate reader (Molecular Devices, Sunnyvale, Calif., USA). Reported optical density is the averaged absorbance for all four wavelengths.

IP1 Functional Assay. Functional activity of the TP receptor was measured by homogenous time-resolved fluorescence (HTRF) (IP-One Tb, Cisbio, Bedford, Mass., USA). QBI-HEK 293A (MP Biomedicals, Solon, Ohio, USA) cells were transfected with human or mouse TP receptor cDNAs cloned into the pcDNA5/TO vector (Invitrogen, Carlsbad, Calif., USA), and stable transformants were selected. Cells were plated at 10,000 cells/well into 384-well plates (Grenier Bio-One, Monroe, N.C., USA) in DMEM containing 4.5 g/L glucose (Invitrogen, Carlsbad, Calif., USA), 10% fetal bovine serum, L-glutamine, and penicillin/streptomycin, followed by incubation for 16 hours at 37° C. with 5% $CO_2$. The culture media were removed and the cells were then incubated for 15 min at 37° C. with 5% $CO_2$ in 10 mM Hepes, 1 mM $CaCl_2$, 0.4 mM $MgCl_2$, 4.2 mM KCl, 146 mM NaCl, 5.5 mM glucose, 50 mM LiCl, pH 7.4 (stimulation buffer) containing varying concentrations of test antagonist. I-BOP ([1S-[1α,2α(Z),3β(1E,3S*),4α]]-7-[3-[3-hydroxy-4-(4-iodophenoxy)-1-butenyl]-7-oxabicyclo[2.2.1]hept-2-yl]-5-heptenoic acid) (Cayman Chemicals, Ann Arbor, Mich., USA) was added at a final concentration of 1.6 nM in stimulation buffer and incubated for 1 hour at 37° C. with 5% $CO_2$. D2-labeled IP1 and Tb-labeled Anti-IP1 cryptate were then added in lysis buffer and incubated for 1 hour at 25° C. Plates were subsequently read on a Spectramax MS microplate reader (Molecular Devices, Sunnyvale, Calif., USA). Data are expressed as the ratio of 665 nm/620 nm fluorescence.

Radioligand Binding Assay. QBI-HEK 293A cells expressing human or mouse TP receptor were grown to confluency in DMEM containing 4.5 g/L glucose (Invitrogen, Carlsbad, Calif., USA), 10% fetal bovine serum, L-glutamine, and penicillin/streptomycin and harvested in phosphate-buffered saline with 1 mM EDTA. The cells were centrifuged and the pellet was homogenized in a glass homogenizer in 20 mM Hepes, 1 mM EGTA, and 0.5 mM DTT with protease inhibitor cocktail. The homogenate was initially centrifuged at 1000×g for 10 minutes at 8° C. to remove cell debris. The homogenate was then centrifuged in a Beckman L8-70M ultracentrifuge (Beckman-Coulter, Brea, Calif., USA) at 21,000 rpm for 30 minutes at 4° C., and the pellet was resuspended in 20 mM Hepes, 1 mM EGTA, 100 mM NaCl. Membrane preparations were normalized to a protein level as determined with a BCA assay (ThermoFisher, Rockland, Ill.) and stored at −80° C. Test antagonists were incubated at 10 different concentrations with 100 µg PVT-WGA SPA beads (PerkinElmer, Waltham, Mass., USA), 62.5 µg membrane and 20 nM $^3$H-SQ29,548 (PerkinElmer, Waltham, Mass., USA) in 50 mM Tris, 4 mM $CaCl_2$, 0.1% ascorbic acid pH 7.5 for 2 hours at 25° C. in 384-well polystyrene plates. Plates were sealed and read on a scintillation counter. Data is presented as percent total binding, with total binding calculated from a minimum of three wells containing membrane, beads, and $^3$H-SQ29,548 without antagonist.

REFERENCES

1. Patani, G. A.; LaVoie, E. J. Bioisosterism: A Rational Approach in Drug Design. *Chem. Rev* 1996, 96, 3147-3176.
2. Boothe, J.; Wilkinson, R.; Kushner, S.; Williams, J. Synthesis of Aureomycin Degradation Products. II. *Journal of the American Chemical Society* 1953, 75, 1732-1733.
3. Hiraga, K. Structures of cyclopentanepolyones. *Chemical & pharmaceutical bulletin* 1965, 13, 1300.
4. Katrusiak, A. Structure of 1,3-cyclopentanedione. *Acta Crystallographica Section C: Crystal Structure Communications* 1990, 46, 1289-1293.
5. Katrusiak, A. Structure of 2-methyl-1,3-cyclopentanedione. *Acta Crystallographica Section C: Crystal Structure Communications* 1989, 45, 1897-1899.
6. Dickinson, R. P.; Dack, K. N.; Long, C. J.; Steele, J. Thromboxane modulating agents. 3. 1H-imidazol-1-ylalkyl- and 3-pyridinylalkyl-substituted 3-[2-[(arylsulfonyl)amino]ethyl]benzenepropanoic acid derivatives as dual thromboxane synthase inhibitor/thromboxane receptor antagonists. *J Med Chem* 1997, 40, 3442-52.
7. Koreeda, M.; Liang, Y.; Akagi, H. Easy generation of the dianions of 3-isobutoxycyclopent-2-en-1-ones and their reactions. *Journal of the Chemical Society, Chemical Communications* 1979, 449-450.
8. Ramachary, D. B.; Kishor, M. Direct amino acid-catalyzed cascade biomimetic reductive alkylations: application to the asymmetric synthesis of Hajos-Parrish ketone analogues. *Organic & Biomolecular Chemistry* 2008, 6, 4176-4187.
9. Tilley, J. W.; Danho, W.; Lovey, K.; Wagner, R.; Swistok, J.; Makofske, R.; Michalewsky, J.; Triscari, J.; Nelson, D.; Weatherford, S. Carboxylic acids and tetrazoles as isosteric replacements for sulfate in cholecystokinin analogs. *Journal of Medicinal Chemistry* 1991, 34, 1125-1136.
10. Henry, J. R.; Marcin, L. R.; McIntosh, M. C.; Scola, P. M.; Davis Harris, G.; Weinreb, S. M. Mitsunobu reactions of n-alkyl and n-acyl sulfonamides-an efficient route to protected amines. *Tetrahedron Letters* 1989, 30, 5709-5712.
11. Peters, L.; Fröhlich, R.; Boyd, A. S. F.; Kraft, A. Noncovalent Interactions between Tetrazole and an N,N'-Diethyl-Substituted Benzamidine. *The Journal of Organic Chemistry* 2001, 66, 3291-3298.
12. Tominey, A. F.; Docherty, P. H.; Rosair, G. M.; Quenardelle, R.; Kraft, A. Unusually Weak Binding Interactions in Tetrazole-Amidine Complexes. *Organic Letters* 2006, 8, 1279-1282.
13. Dogne, J.; Hanson, J.; Leval, X.; Pratico, D.; Pace-Asciak, C.; Drion, P.; Pirotte, B.; Ruan, K. From the design to the clinical application of thromboxane modulators. *Current Pharmaceutical Design* 2006, 12, 903-923.
14. Yamamoto, Y.; Kamiya, K.; Terao, S. Modeling of human thromboxane A2 receptor and analysis of the receptor-ligand interaction. *J Med Chem* 1993, 36, 820-5.
15. Suzuki, Y., et al., Prophylactic effects of the histamine H1 receptor antagonist epinastine and the dual thromboxane A2 receptor and chemoattractant receptor-homologous molecule expressed on the Th2 cells antagonist ramatroban on allergic rhinitis model in mice, Biol. Pharm. Bull. 2011; 34(4); 507-10.
16. Xu, S. et al., The thromboxane receptor antagonist S18886 attenuates renal oxidant stress and proteinuria in diabetic apolipoprotein E-deficient mice, Diabetes, 2006 January; 55(1):110-9
17. Dogne J. M., et al. Thromboxane A2 inhibition: therapeutic potential in bronchial asthma, Am. J. Respir. Med. 2002; 1(1):11-17
18. Ballatore, C. et al, Cyclopentane-1,3-dione: a novel isostere for the carboxylic acid functional group. Application to the design of potent thromboxane (A2) receptor antagonists, J. Med. Chem. 2011 Oct. 13:54(19):6969-83

What is claimed:
1. A compound of formula I:

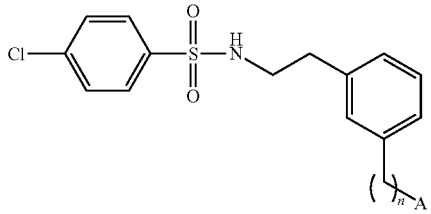

wherein
A is

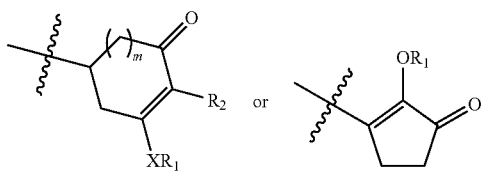

n is 0, 1, or 2;
m is 0 or 1;
$R_1$ is H or $C_{1-6}$alkyl and
$R_2$ is H, $C_{1-6}$alkyl, substituted or unsubstituted aryl, or substituted or unsubstituted heteroaryl; and
X is O or N;
or a tautomer or pharmaceutically acceptable salt form thereof.

2. The compound of claim 1, wherein A is

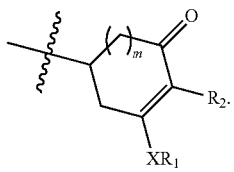

3. The compound of claim 2, wherein m is 0.
4. The compound of claim 1, X is O.
5. The compound of claim 1, wherein n is 1.
6. The compound of claim 1, wherein $R_1$ is H.
7. The compound of claim 1, wherein $R_2$ is $C_{1-6}$alkyl.
8. The compound of claim 7, wherein $R_2$ is methyl.
9. The compound of claim 7, wherein $R_2$ is ethyl.
10. The compound of claim 7, wherein $R_2$ is propyl.
11. The compound of claim 7, wherein $R_2$ is isopropyl.
12. The compound of claim 7, wherein $R_2$ is —$CH_2$-cyclopropyl.
13. The compound of claim 7, wherein $R_2$ is cyclohexyl.
14. The compound of claim 1, wherein $R_2$ is substituted or unsubstituted aryl.
15. The compound of claim 1, wherein $R_2$ is H.
16. The compound of claim 2, wherein m is 1.
17. The compound of claim 16, wherein $R_2$ is cyclohexyl.
18. The compound of claim 1, wherein A is

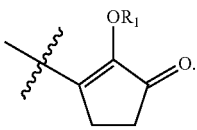

19. The compound of claim 18, wherein $R_1$ is H.
20. The compound of claim 1, wherein the compound is of formula IA

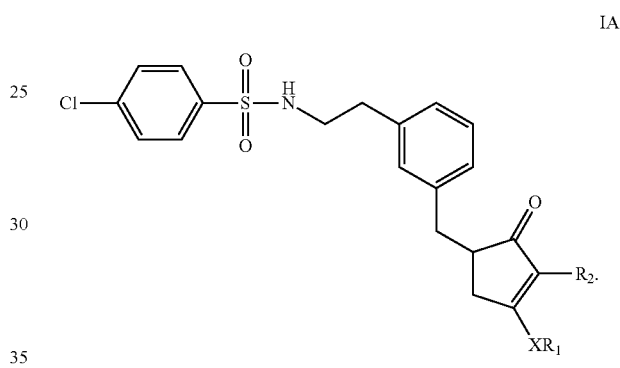

21. The compound of claim 20, wherein $R_1$ is H.
22. The compound of claim 20, wherein $R_1$ is $C_{1-6}$alkyl.
23. The compound of claim 20, wherein $R_1$ is H and $R_2$ is H.
24. The compound of claim 20, wherein $R_1$ is H and $R_2$ is $C_{1-6}$alkyl.
25. The compound of claim 24, wherein $R_2$ is methyl, ethyl, propyl, isopropyl, or —$CH_2$-cyclopropyl.
26. The compound of claim 1, wherein X is N.
27. A pharmaceutical formulation comprising a compound according to claim 1 and a pharmaceutically acceptable carrier or diluent.
28. A method of treating thrombus, Alzheimer's disease, diabetic nephropathy, bronchial asthma, or allergic rhinitis in a patient comprising administering to the patient a therapeutically effective amount of a pharmaceutical formulation according to claim 27.

* * * * *